US012653763B2

(12) United States Patent
Goutayer et al.

(10) Patent No.: US 12,653,763 B2
(45) Date of Patent: Jun. 16, 2026

(54) SHELL-FREE STABLE DISPERSION

(71) Applicant: CAPSUM, Marseilles (FR)

(72) Inventors: Mathieu Goutayer, Saint Malo (FR); Julie Bacon, Marseilles (FR)

(73) Assignee: CAPSUM, Marseilles (FR)

( * ) Notice: Subject to any disclaimer, the term of this patent is extended or adjusted under 35 U.S.C. 154(b) by 651 days.

(21) Appl. No.: 17/998,701

(22) PCT Filed: May 21, 2021

(86) PCT No.: PCT/EP2021/063598

§ 371 (c)(1),
(2) Date: Nov. 14, 2022

(87) PCT Pub. No.: WO2021/234135

PCT Pub. Date: Nov. 25, 2021

(65) Prior Publication Data

US 2023/0233422 A1 Jul. 27, 2023

(30) Foreign Application Priority Data

May 21, 2020 (FR) ....................................... 2005408

(51) Int. Cl.
*A61K 8/06* (2006.01)
*A61K 8/92* (2006.01)
*A61Q 5/00* (2006.01)

(52) U.S. Cl.
CPC .................. *A61K 8/06* (2013.01); *A61K 8/92* (2013.01); *A61Q 5/00* (2013.01); *A61K 2800/33* (2013.01)

(58) Field of Classification Search
CPC ...... A61K 2800/33; A61K 8/042; A61K 8/06; A61K 8/062; A61K 8/375; A61K 8/92; A61K 2800/43; A61K 2800/437; A61K 8/04; A61K 8/11; A61K 8/361; A61K 8/898; A61Q 19/00; A61Q 5/00; A61Q 1/02
See application file for complete search history.

(56) References Cited

U.S. PATENT DOCUMENTS

| | | | | |
|---|---|---|---|---|
| 5,783,657 | A | 7/1998 | Pavlin et al. | |
| 5,874,069 | A | 2/1999 | Mendolia et al. | |
| 5,919,441 | A | 7/1999 | Mendolia et al. | |
| 5,981,680 | A | 11/1999 | Petroff et al. | |
| 6,051,216 | A | 4/2000 | Barr et al. | |
| 8,685,375 | B2 | 4/2014 | Arditty et al. | |
| 9,277,759 | B2 | 3/2016 | Bibette et al. | |
| 9,993,398 | B2 | 6/2018 | Goutayer et al. | |
| 10,300,006 | B2 | 5/2019 | Goutayer et al. | |
| 11,077,032 | B2 | 8/2021 | Goutayer et al. | |
| 2004/0137020 | A1* | 7/2004 | De La Poterie | A61Q 1/10 424/401 |
| 2020/0129413 | A1 | 4/2020 | Pujol et al. | |
| 2021/0039059 | A1 | 2/2021 | Pafumi et al. | |
| 2021/0077362 | A1 | 3/2021 | Rehault et al. | |

FOREIGN PATENT DOCUMENTS

| | | | | | |
|---|---|---|---|---|---|
| EP | 2189081 | A2 | | 5/2010 | |
| FR | 2792190 | A1 | | 10/2000 | |
| FR | 2999921 | A1 | | 6/2014 | |
| FR | 3041251 | A1 | | 3/2017 | |
| JP | H02295912 | A | | 12/1990 | |
| WO | 0247619 | A2 | | 6/2002 | |
| WO | 02056847 | A1 | | 7/2002 | |
| WO | 2010063937 | A1 | | 6/2010 | |
| WO | 2012120043 | A2 | | 9/2012 | |
| WO | WO2012120043 | | * | 9/2012 | B01J 13/10 |
| WO | 2015055748 | A1 | | 4/2015 | |
| WO | 2017046305 | A1 | | 3/2017 | |
| WO | 2018167309 | A1 | | 9/2018 | |
| WO | 2019002308 | A1 | | 1/2019 | |
| WO | WO2019002308 | | * | 1/2019 | A61K 8/92 |
| WO | 2019145424 | A1 | | 8/2019 | |

OTHER PUBLICATIONS

WO2012120043 translation (Year: 2012).*
Search Report for French Application No. 2005408 dated Feb. 2, 2021.
Search Report for International Application No. PCT/EP2021/063598 dated Jun. 24, 2021.

* cited by examiner

*Primary Examiner* — Audrea B Coniglio
(74) *Attorney, Agent, or Firm* — McDonald Hopkins LLC

(57) ABSTRACT

A dispersion comprises a dispersed phase comprising drops and a continuous aqueous phase, preferably in gel form, wherein the drops comprise a fatty phase comprising at least one lipophilic gelling agent, wherein: the fatty phase has a melting point between 50° C. and 100° C., preferably between 60° C. and 90° C., and, at room temperature and atmospheric pressure, meets the following physicochemical criteria: a hardness (x) of between 2 and 14 N, preferably between 2.5 and 12 N, more preferably between 3 and 9 N, and most preferably between 4 and 6 N; and an adhesiveness (y) greater than or equal to −2 N, and better still, greater than or equal to −1 N, and in particular greater than or equal to −0.6 N; and the dispersion does not comprise amodimethicone.

18 Claims, 7 Drawing Sheets

SHELL-FREE STABLE DISPERSION

CROSS-REFERENCE TO RELATED APPLICATIONS

This is a National Stage application of PCT international application PCT/EP2021/063598, filed on May 21, 2021, which claims the priority of French Patent Application No. 2005408, Filed May 21, 2020, both of which are incorporated herein by reference in their entirety.

The object of the present invention is stable oil-in-water dispersions comprising a continuous aqueous phase and drops, in particular macroscopic drops, of a dispersed fatty phase comprising at least one lipophilic gelling agent. The object is also compositions, in particular cosmetic compositions, containing said dispersions, as well as their uses in the cosmetic field.

To date, there are dispersions in the form of a direct emulsion, such as those described in US 2004/137020 and EP 2 189 081. However, the dispersed phases of these dispersions are not in the form of macroscopic drops and are so hard that the sensoriality and/or comfort on application are not satisfactory, especially in the presence of dispersed phases in the form of macroscopic drops.

There are also stable dispersions of drops of a fatty phase dispersed in a continuous aqueous phase, as described in WO2017046305. These dispersions are obtained using a microfluidic method and their kinetic stability is ensured thanks to the presence of a shell derived from a complex interfacial coacervation reaction which relies in particular on a lipophilic silicone cationic polymer, amodimethicone. The drops of the dispersed fatty phase of these dispersions are macroscopic, i.e. visible to the naked eye, and give said dispersions an attractive aesthetic appearance sought by the consumer. This property is all the more interesting as the shell of the drops is very thin and no resistance attached to the breaking of the shell is felt by the user at the time of application on a keratinous material, nor is any residual deposit of said observed shell. This is called an evanescent shell.

There is a growing consumer demand for cosmetic compositions without silicone compounds because of their environmental impact, as they are not biodegradable, and/or because of their suspected health hazards.

Furthermore, the inventors have observed that the presence of amodimethicone can sometimes lead to problems of compatibility with other raw materials and/or phenomena of aggregation of the drops with each other, adhesion of the drops to the packaging, and/or spherical defects of the drops, which for obvious reasons is not desirable. Indeed, such disadvantages may impact the stability of the dispersion and/or the homogeneity of delivery of the different phases constituting the dispersion and/or the visual and aesthetic appearance of the dispersion, or even its sensoriality when applied to the skin, and these drawbacks are exacerbated as the diameter of the drops increases. Without wishing to be bound by any theory, the Applicant believes that the above-mentioned sphericity defect of the drops may be related to a decrease in the elasticity of the dispersed fatty phase due to the presence of amodimethicone.

There is therefore a need for new dispersions comprising drops of a dispersed fatty phase, particularly of macroscopic size, in a continuous aqueous phase and which remain satisfactory in terms of kinetic stability, sensoriality, and comfort on application, despite the absence of amodimethicone and therefore of shell.

Thus, the present invention relates to an oil-in-water dispersion comprising, or even containing, a dispersed phase comprising drops and a continuous aqueous phase, preferably in gel form, wherein the drops comprise a fatty phase comprising at least one lipophilic gelling agent and optionally at least one oil, wherein:

- the fatty phase has a melting point between 50° C. and 100° C., preferably between 60° C. and 90° C., and, at room temperature and atmospheric pressure, meets the following physicochemical criteria:
- a hardness (x) of between 2 and 14 N, preferably between 2.5 and 12 N, more preferably between 3 and 9 N, and most preferably between 4 and 6 N; and
- an adhesiveness (y) greater than or equal to −2 N, and better still, greater than or equal to −1 N, and in particular greater than or equal to −0.6 N; and
- the dispersion does not comprise amodimethicone.

Preferably, the fatty phase of a dispersion according to the invention also has a cohesiveness (z) of less than or equal to 40, preferably less than or equal to 35, and better still, greater than or equal to 30.

As can be seen from the examples below, and unexpectedly, the use of a dispersed fatty phase with the above physicochemical properties makes it possible to obtain dispersions, particularly macroscopic dispersions, with satisfactory or even improved performance in terms of kinetic stability and therefore visual and aesthetic appearance, ease and comfort of application to the skin, despite the absence of amodimethicone and therefore of a shell.

In particular, the inventors have observed that a dispersion according to the invention presents satisfactory, or even improved, performances in terms of non-aggregation of the drops with each other, non-adhesion of the drops to the packaging, and in terms of comfort and ease of application to the skin.

Given the absence of amodimethicone, a dispersion according to the invention also allows more freedom as to the compounds and/or their contents, in particular active ingredients, that can be encapsulated.

The terms "stable" and "kinetic stability" refer, within the meaning of the present invention, at room temperature and atmospheric pressure, to the absence of creaming or sedimentation of the drops of dispersed phase in the continuous phase, the absence of opacification of the continuous aqueous phase, the absence of aggregation of the drops with each other, and in particular the absence of coalescence or Ostwald ripening of the drops between them, the absence of adhesion of the drops to the packaging and the absence of leakage of materials from the dispersed phase to the continuous phase, or vice versa, for a dispersion according to the invention over a period of time greater than or equal to 1 month, preferably greater than or equal to 3 months, and better still, greater than or equal to 6 months.

By "gelling agent" is meant, within the meaning of the present invention, an agent making it possible to increase the viscosity of the phase without said gelling agent, and preferably to achieve a final viscosity of the phase thus gelled of greater than 20,000 mPa·s, preferably greater than 50,000 mPa·s, better still greater than 100,000 mPa·s, and very particularly greater than 200,000 mPa·s.

"Macroscopic", or "macroscopic drop", or "macroscopic dispersion" means, in the sense of the present invention, drops of dispersed fatty phase visible to the naked eye, as opposed to microscopic drops not visible to the naked eye. Thus, preferably, in a dispersion according to the invention:

- the drops having a diameter greater than or equal to 100 μm, or even greater than or equal to 200 μm, or better still, greater than or equal to 300 μm, in particular greater than or equal to 400 μm, preferably greater than or equal to 500 μm, or even greater than or equal to 1,000 μm, or even between 100 μm and 3,000 μm, better between 200 μm and 2,000 μm, in particular between 300 μm and 1,000 μm, or better still, between 500 μm and 3,000 μm, preferably between 1,000 μm and 2,000 μm, in particular between 800 μm and 1,500 μm, represent a volume greater than or equal to 60%, or greater than or equal to 70%, preferably greater than or equal to 80%, and better still, greater than or equal to 90%, of the total volume of the dispersed phase, and/or;

at least 60%, or even at least 70%, preferably at least 80%, and better still at least 90%, of the drops have an average diameter greater than or equal to 100 μm or even greater than or equal to 200 μm, and better still, greater than or equal to 300 μm, in particular greater than or equal to 400 μm, preferably greater than or equal to 500 μm, or even greater than or equal to 1,000 μm, or even between 100 μm and 3,000 μm, and better still, between 200 μm and 2,000 μm, in particular between 300 μm and 1,000 μm, better between 500 μm and 3,000 μm, preferably between 1,000 μm and 2,000 μm, in particular between 800 μm and 1,500 μm.

The determination of the volume of drops with a particular diameter in relation to the total volume of the dispersed phase is a matter of general knowledge of the person skilled in the art, especially with regard to the diameter measurement method described below.

A dispersion according to the invention can be described as a macroscopically inhomogeneous mixture of two immiscible phases, in particular when the drops are macroscopic. In other words, in a dispersion according to the invention, each of the phases can be individually discerned, particularly with the naked eye.

In the context of the present invention, the above-mentioned dispersions may be referred to as "emulsions". With regard to the nature of the phases, an emulsion according to the invention is an oil-in-water type emulsion (or direct emulsion), the dispersed fatty phase and the continuous aqueous phase being immiscible with each other at room temperature and atmospheric pressure. Thus, the solubility of the dispersed fatty phase in the continuous aqueous phase is advantageously less than 5% by weight, and vice versa.

According to another embodiment, a dispersion according to the invention is a simple emulsion i.e. containing only a continuous aqueous phase and a dispersed fatty phase. In other words, a dispersion according to the invention is not a multiple emulsion, in particular a double emulsion, for example of the water-in-oil-in-water type.

According to another embodiment, a dispersion according to the invention does not comprise a surfactant.

According to one embodiment, a dispersion according to the invention does not comprise glyceryl trioctanoate, glycerol tricaprylate/caprate, or a mixture thereof.

According to one embodiment, a dispersion according to the invention does not comprise:

dextrin ester and fatty acid(s), in particular dextrin palmitate(s), and/or optionally hydrophobically treated silica, e.g. fumed silica, and/or Acrylates/C10-30 Alkyl Acrylate Crosspolymer, in particular Pemulen™ EZ-4U Polymeric Emulsifier from Lubrizol; and/or Cetyl Ethylhexanoate.

Preferably, the drops have an apparent monodispersity (i.e. they are perceived by the eye as spheres identical in diameter).

The drops are advantageously substantially spherical.

The drops of a dispersion according to the invention are free of a shell or membrane, in particular a polymeric membrane or a membrane formed by interfacial polymerisation. In particular, the drops of a dispersion according to the invention are not stabilised with a coacervate membrane (anionic polymer (carbomer)/cationic polymer (amodimethicone) type). In other words, the contact between the continuous aqueous phase and the dispersed fatty phase is direct.

Thus, according to one embodiment, a dispersion according to the invention does not comprise a shell, in particular a shell formed by a layer of coacervate interposed between the dispersed fatty phase and the continuous aqueous phase.

In particular, a dispersion according to the invention does not comprise (is devoid of) a lipophilic cationic polymer of the following formula:

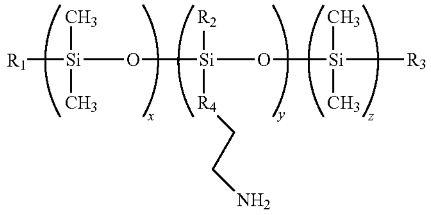

in which:

$R_1$, $R_2$ and $R_3$, independently of each other, represent OH ou $CH_3$;

$R_4$ represents a $—CH_2—$ group or an —X—NH— group in which X is a divalent C3 or C4 alkylene radical;

x is an integer between 10 and 5,000, preferably between 30 and 1,000, and more preferably between 80 and 300;

y is an integer between 1 and 1000, in particular between 2 and 1000, preferably between 4 and 100, and more preferably between 5 and 20; and z is an integer between 0 and 10, preferably between 0 and 1, and more preferably equal to 1.

The drops differ from solid capsules, i.e. capsules with a solid shell (or "membrane"), such as for example those described in WO 2010/063937, and capsules with an evanescent shell, such as for example those described in WO2012120043.

According to the invention, the pH of a dispersion is typically between 4.0 and 8.0, in particular between 5.0 and 7.0.

Temperature and Pressure

Unless otherwise stated, all the following is considered to be at room temperature (e.g. T=25° C.±2° C.) and atmospheric pressure (760 mm Hg, i.e. $1.013*10^5$ Pa or $10^{13}$ mbar).

Viscosity

The viscosity of a dispersion according to the invention or of at least one of its phases can vary significantly, which makes it possible to obtain various textures. The viscosity is measured at room temperature and at room pressure according to the method described in WO2017046305.

According to one embodiment, a dispersion according to the invention has a viscosity of from 1 mPa·s to 500,000 mPa·s, preferably from 10 mPa·s to 300,000 mPa·s, more preferably from 400 mPa·s to 100,000 mPa·s, and more particularly from 1,000 mPa·s to 30,000 mPa·s, as measured at 25° C. according to the method described above.

Continuous Aqueous Phase

As mentioned above, the dispersions according to the invention comprise an continuous aqueous phase, preferably in the form of a gel, in particular a gel with a viscosity suitable for suspending the drops and thus contributing to the kinetic stability and visual attractiveness of a dispersion according to the invention.

Advantageously, the continuous aqueous phase is not solid at room temperature and room pressure, i.e. it is capable of flowing under its own weight.

According to one embodiment, the aqueous phase has a viscosity of between 400 mPa·s and 100,000 mPa·s, preferably between 800 mPa·s and 30,000 mPa·s, as measured at 25° C. by the method described above.

The continuous phase of a dispersion according to the invention comprises water.

In addition to distilled or deionised water, water suitable for the invention may also be natural spring water or floral water.

According to one embodiment, the percentage by weight of water in the continuous aqueous phase is at least 30%, preferably at least 40%, in particular at least 50%, and better still at least 60%, in particular between 70% and 98%, and preferably between 75% and 95%, relative to the total weight of said continuous phase.

The continuous aqueous phase of a dispersion according to the invention may further comprise at least one base. It may comprise a single base or a mixture of several different bases. The presence of at least one base in said continuous aqueous phase contributes in particular to increasing the viscosity of the latter.

In one embodiment, the base present in the aqueous phase is a mineral base.

According to one embodiment, the mineral base is selected from the group consisting of alkali metal hydroxides and alkaline earth metal hydroxides.

Preferably, the mineral base is an alkali metal hydroxide, especially NaOH.

In one embodiment, the base present in the aqueous phase is an organic base. Examples of organic bases are ammonia, pyridine, triethanolamine, aminomethylpropanol, or triethylamine.

A dispersion according to the invention may comprise from 0.01% to 10% by weight, preferably from 0.01% to 5% by weight, and preferably from 0.02% to 1% by weight of base, preferably mineral base, and in particular NaOH, relative to the total weight of said dispersion.

Fatty Phase

The dispersed fatty phase of a dispersion according to the invention has a melting point between 50° C. and 100° C., preferably between 60° C. and 90° C.

The melting point of the fatty phase can be measured using a differential scanning calorimeter (DSC), for example the calorimeter sold as "DSC Q2000" by TA Instruments. The sample preparation and measurement protocols are as follows: A 5 mg sample of the test sample, previously heated to 80° C. and taken under magnetic stirring with a heated spatula, is placed in a hermetically sealed aluminium capsule, or crucible. Two tests are carried out to ensure the reproducibility of the results. The measurements are taken on the above-mentioned calorimeter. The furnace is flushed with nitrogen. Cooling is provided by the RCS 90 heat exchanger. The sample is then subjected to the following protocol by first being heated to 20° C., then subjected to a first temperature rise from 20° C. to 130° C. at a heating rate of 5° C./minute, then cooled from 130° C. to −80° C. at a cooling rate of 5° C./minute and finally subjected to a second temperature rise from −80° C. to 130° C. at a heating rate of 5° C./minute. During the second temperature rise, the variation of the difference in power absorbed by the empty crucible and the crucible containing the sample is measured as a function of temperature. The melting point of the compound is the value of the temperature corresponding to the peak of the curve representing the variation of the power input difference with temperature. The melting point is the temperature at which 95% of the sample has melted.

The dispersed fatty phase of a dispersion according to the invention must satisfy at least the following two physicochemical criteria of hardness and adhesiveness:

- a hardness (x) of between 2 N and 14 N, preferably between 2.5 N and 12 N, in particular between 3 and 9 N, and better still between 4 and 6 N. The hardness (or firmness) corresponds to the maximum compression force measured in Newton. In relation to a dispersion according to the invention, the hardness (x) is an indicator of the sensory feel of a dispersion upon application to a keratinous material, in particular the skin. On the one hand, the hardness must not be too low to ensure that the dispersed fatty phase drops have sufficient mechanical resistance, in particular to shearing and/or mechanical stresses related, for example, to the manufacture and packaging of the dispersion and/or its transport, and thus to ensure that the dispersion has satisfactory kinetic stability, particularly in the presence of non-airless packaging. On the other hand, the hardness should not be too great so as not to degrade the sensoriality, in particular the comfort and ease of application of the dispersion when applied to the skin. The above is exacerbated the larger the diameter of the dispersed fatty phase drops in a dispersion.
- an adhesiveness (y) greater than or equal to −2 N, better greater than or equal to −1 N and in particular greater than or equal to −0.6 N. The adhesiveness represents the work required to overcome the attractive forces between the surface of the product and the material with which it is in contact (for example, the total force required to separate the measuring tool from the sample). In relation to a dispersion according to the invention, the adhesiveness criterion (y) is an indicator of the kinetic stability of the dispersion with regard to the phenomena of adhesion of the drops to the packaging wall.

The dispersed fatty phase of a dispersion according to the invention advantageously has a cohesiveness (z) of less than or equal to 40, preferably less than or equal to 35, and better still, greater than or equal to 30. Preferably, the dispersed fatty phase of a dispersion according to the invention advantageously has a cohesiveness (z) of greater than or equal to 15, preferably greater than or equal to 20, and better still, greater than or equal to 25. Advantageously, the dispersed fatty phase of a dispersion according to the invention has a cohesiveness (z) of between 15 and 40, preferably between 20 and 35, and better still, between 20 and 30. Cohesiveness refers to how well the tested product resists the second deformation, relative to how it behaved during the first deformation. Cohesiveness corresponds to the area of the second curve (Area. 2) on the surface of the first curve (Area 1) (i.e. Area. 2/Area. 1). In other words, cohesiveness represents the strengths within the sample being tested. Thus, strong bonds within the gel will allow a totally reversible deformation during the first compression which will induce a force A2 identical to the force A1, and thus a 100% cohesiveness. Consequently, the stronger the cohesiveness, the more deformable the gel. The lower the cohesiveness, the more brittle the gel (weak bonds, no resistance to stress). In relation to a dispersion according to the invention, the cohesiveness criterion (z) is an indicator of the kinetic stability of the dispersion with regard to the phenomena of aggregation, or even coalescence, of the dispersed phase drops between them. Cohesiveness is the property of the drops to stick to themselves. Thus, a minimum of cohesiveness is needed to ensure the "gelled" character of the drops, but not too much to prevent the gelled drops from sticking together.

Hardness, adhesion and cohesiveness measurements are obtained using the Shimadzu EZ-X texturometer and the texturometer protocol described below:

the test sample is placed in a 40 mm diameter mould filled to 75% of its height.

The mobile used is a cylindrical acrylic mobile with a diameter of 12.7 mm. The movement of the mobile comprises 4 steps:

1) a 1st step after automatic detection of the sample surface where the mobile moves at the measurement speed of 1 mm/s, and penetrates the sample to a penetration depth of 5 mm, the software notes the value of the maximum force reached
2) a second step, called withdrawal, at a speed of 1 mm/s, where the mobile returns to its initial position and rises by 5 mm; and the withdrawal energy of the probe (negative force) is noted
3) a 3rd step repeating the same action 1) described above, and
4) a 4th step repeating the same action 2) described above.

This combination of physicochemical criteria constitutes a non-obvious compromise characterising a brittle but not very adhesive and not very elastic anhydrous gel. As can be seen from the examples below, this combination of physicochemical criteria makes it possible to obtain dispersions, particularly macroscopic dispersions, with satisfactory or even improved performance in terms of kinetic stability, and therefore visual and aesthetic rendering, and sensoriality, particularly comfort and ease of application to the skin, despite the absence of amodimethicone and therefore of a shell.

With regard to hardness, the hardness values in N, obtained by the above-mentioned measurement method, can easily be converted into Pa, for example with regard to the surface of the above-mentioned 12.7 mm cylindrical acrylic mobile.

Typically, 1 MPa is equivalent to 1 $N/mm^2$. Also, to convert the measured hardness values according to the invention into N, it is sufficient to divide them by the surface of the probe. For example, using a probe as above with a diameter of 12.7 mm, its surface area is equal to $S=\pi\times(12.7/2)^2=126.68\ mm^2$. To obtain the hardness values in MPa, the values measured with this probe should be divided by 126.68.

For the above measurements, the above-mentioned Shimadzu EZ-X texturometer works in combination with the TRAPEZIUM X software.

The dispersed fatty phase drops of a dispersion according to the invention are preferably based on a viscoelastic gel with an elastic modulus greater than the viscous modulus. The drops do not flow under their own weight, but can be easily deformed by pressure, for example with a finger. Thus, their consistency is similar to that of butter, with a malleable and grippable character. The drops can be easily spread by hand, especially on keratinous material, especially the skin.

The dispersed fatty phase of a dispersion according to the invention comprises at least one lipophilic gelling agent. It is essentially the combination of at least one lipophilic gelling agent and at least one oily solvent that enable the dispersed fatty phase of a dispersion according to the invention to satisfy the above-mentioned physicochemical criteria x and y, or even z.

Lipophilic Gelling Agent

Advantageously, a lipophilic gelling agent is a heat-sensitive gelling agent, i.e. one which reacts to heat, and in particular is a gelling agent which is solid at room temperature and liquid at a temperature above 50° C., preferably above 60° C., and more preferably above 70° C. Preferably, a lipophilic heat-sensitive gelling agent according to the invention has a melting point between 50° C. and 130° C., and preferably between 60° C. and 120° C.

The lipophilic gelling agent according to the invention may be chosen from organic or inorganic, polymeric or molecular lipophilic gelling agents; fats that are solid at ambient temperature and pressure; and mixtures thereof.

Organic or Inorganic, Polymeric or Molecular Lipophilic Gelling Agent(s)

As a lipophilic mineral gelling agent, mention may be made of clays which may be modified, such as hectorites modified with a $C_{10}$ to $C_{22}$ ammonium chloride, such as hectorite modified with di-stearyl di-methyl ammonium chloride, such as, for example, that marketed under the name of Bentone 38VÒ by the company ELEMENTIS. Other examples include distearyldimethylammonium chloride-modified hectorite, also known as quaternium-18 bentonite, such as the products marketed or manufactured as Bentone 34 by Rheox, Claytone XL, Claytone 34 and Claytone 40 marketed or manufactured by Southern Clay, modified clays known as benzalkonium and quaternium-18 bentonites and marketed or manufactured as Claytone HT, Claytone GR and Claytone PS by Southern Clay, clays modified with stearyldimethylbenzoylammonium chloride, known as steralkonium bentonites, such as the products marketed or manufactured under the names Claytone APA and Claytone AF by Southern Clay, and Baragel 24 marketed or manufactured by Rheox Another example is fumed silica, which may be treated with a hydrophobic surface treatment, with a particle size of less than 1 μm. It is indeed possible to chemically modify the silica surface, by chemical reaction generating a decrease in the number of silanol groups present on the silica surface. In particular, silanol groups can be substituted with hydrophobic groups, resulting in a hydrophobic silica.

The hydrophobic groups can be:

trimethylsiloxyl groups, which are obtained in particular by treating fumed silica in the presence of hexamethyldisilazane. Silicas treated in this way are referred to as "Silica silylate" according to the CTFA (8th edition, 2000). They are for example marketed under the references Aerosil R812Ò by DEGUSSA, CAB-O-SIL TS-530Ò by CABOT; or dimethylsilyloxyl or polydimethylsiloxane groups, which are obtained in particular by treating fumed silica in the presence of polydimethylsiloxane or dimethyldichlorosilane. Silicas treated in this way are referred to as "Silica dimethyl silylate" according to the CTFA (8th edition, 2000). They are for example marketed under the references Aerosil R972Ò, and Aerosil R974Ò by DEGUSSA, CAB-O-SIL TS-610Ò and CAB-O-SIL TS-720Ò by CABOT.

In particular, the hydrophobic fumed silica has a particle size that can be nano to micrometer, for example from about 5 to 200 nm.

The polymeric organic lipophilic gelling agents are for example the partially or totally cross-linked elastomeric organopolysiloxanes with a three-dimensional structure, such as those marketed under the names of KSG6Ò, KSG16Ò and KSG18Ò by the company SHIN-ETSU, Trefil E-505CÒ and Trefil E-506CÒ by the company DOW-CORNING, SR-CYCÒ, SR DMF10Ò, SR-DC556Ò, SR 5CYC gelÒ, SR DMF 10 gelÒ and SR DC 556 gelÒ by the company GRANT INDUSTRIES, SF 1204Ò and JK 113Ò by the company GENERAL ELECTRIC; ethyl cellulose such as that sold under the name EthocelÒ by the company DOW CHEMICAL; galactommanans containing from one to six, and in particular from two to four, hydroxyl groups per ose, substituted by a saturated or unsaturated alkyl chain, such as guar gum alkylated by C1 to C6, and in particular C1 to C3, alkyl chains, and mixtures thereof. Block copolymers of the "diblock", "triblock" or "radial" type, such as polystyrene/polyisoprene, polystyrene/polybutadiene, such as those marketed under the name Luvitol HSB® by the company BASF, of the polystyrene/copoly(ethylene-propylene) type, such as those marketed under the name Kraton® by the company SHELL CHEMICAL CO, or even of the polystyrene/copoly(ethylene-butylene) type mixtures of triblock and radial (star) copolymers in isododecane such as those marketed by the company PENRECO under the name Versagel®, such as the mixture of triblock butylene/ethylene/styrene copolymer and ethylene/propylene/styrene star copolymer in isododecane (Versagel M 5960).

According to one embodiment, the gelling agents usable according to the invention may be selected from the group consisting of polyacrylates; sugar/polysaccharide and fatty acid(s) esters, in particular dextrin and fatty acid(s) esters, glycerol and fatty acid(s) esters or inulin and fatty acid(s) esters; polyamides, and mixtures thereof.

As lipophilic gelling agents, mention may also be made of polymers with a weight-average molecular mass of less than 100,000, comprising a) a polymeric backbone having hydrocarbon repeat units provided with at least one heteroatom, and optionally b) at least one pendant fatty chain and/or at least one optionally functionalized terminal fatty chain, having from 6 to 120 carbon atoms and being bonded to these hydrocarbon units, as described in applications WO 02/056847, WO 02/47619, in particular polyamide resins (in particular comprising alkyl groups having from 12 to 22 carbon atoms) such as those described in U.S. Pat. No. 5,783,657.

An example of a polyamide resin that can be used according to the present invention is UNICLEAR 100 VG® marketed by the company ARIZONA CHEMICAL.

Alternatively, silicone polyamides of the polyorganosiloxane type such as those described in U.S. Pat. Nos. 5,874,069, 5,919,441, 6,051,216 and 5,981,680 may be used.

These silicone polymers can belong to the following two families:

- polyorganosiloxanes with at least two groups capable of establishing hydrogen interactions, these two groups being located in the polymer chain, and/or
- polyorganosiloxanes containing at least two groups capable of establishing hydrogen interactions, these two groups being located on grafts or branches.

Lipophilic gelling agents which may be used in the present invention include fatty acid dextrin esters, such as dextrin palmitates. According to one embodiment, the ester of dextrin and fatty acid(s) according to the invention is a mono- or poly-ester of dextrin and at least one fatty acid corresponding to the following formula (II):

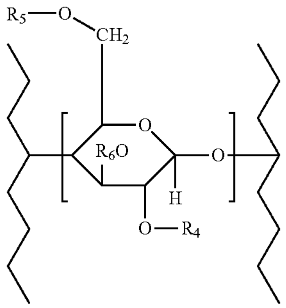

(II)

wherein:

n is an integer from 2 to 200, preferably from 20 to 150, and in particular from 25 to 50, the radicals R4, R5 and R6, which may be identical or different, are chosen from hydrogen or an acyl group —CORa in which the radical Ra represents a linear or branched, saturated or unsaturated hydrocarbon radical having from 5 to 50, preferably from 5 to 25, carbon atoms, with the proviso that at least one of said R4, R5 or R6 radicals is other than hydrogen.

Examples of dextrin fatty acid esters are dextrin palmitates, dextrin myristates, dextrin palmitates/ethylhexanoates and mixtures thereof. Examples include dextrin esters of fatty acid(s) marketed under the names Rheopearl® KL2 or D2 (INCI name: dextrin palmitate), Rheopearl® TT2 (INCI name: dextrin palmitate ethylhexanoate), and Rheopearl® MKL2 (INCI name: dextrin myristate) by the company Miyoshi Europe. Among the lipophilic gelling agents that can be used in the present invention, mention may also be made of the esters of inulin and fatty acid(s) marketed under the names Rheopearl® ISK2 or Rheopearl® ISL2 (INCI name: Stearoyl Inulin) by the company Miyoshi Europe.

Among the lipophilic gelling agents which can be used in the present invention, mention may also be made of polyacrylates resulting from the polymerisation of $C_{10}$-$C_{30}$ alkyl acrylate(s), preferably $C_{14}$-$C_{24}$ alkyl acrylate(s), and even more preferably $C_{18}$-$C_{22}$ alkyl acrylate(s). According to one embodiment, the polyacrylates are polymers of acrylic acid esterified with a fatty alcohol whose saturated carbon chain comprises from 10 to 30 carbon atoms, preferably from 14 to 24 carbon atoms, or a mixture of said fatty alcohols. Preferably, the fatty alcohol comprises 18 carbon atoms or 22 carbon atoms. Polyacrylates particularly include stearyl polyacrylate and behenyl polyacrylate. Preferably, the gelling agent is stearyl polyacrylate or behenyl polyacrylate. Examples include polyacrylates marketed under the names Interlimer® (INCI name: Poly C10-C30 alkyl acrylate), including Interlimer® 13.1 and Interlimer® 13.6, by Airproducts.

Among the lipophilic gelling agents which may be used in the present invention, mention may also be made of esters of glycerol and fatty acid(s), in particular a mono-, di- or triester of glycerol and fatty acid(s). Typically, said ester of glycerol and fatty acid(s) may be used alone or in a mixture. According to the invention, this may be an ester of glycerol and a fatty acid or an ester of glycerol and a mixture of fatty acids. According to one embodiment, the fatty acid is selected from the group consisting of behenic acid, isooctadecanoic acid, stearic acid, eicosanoic acid, and mixtures thereof.

In one embodiment, the glycerol fatty acid ester has the following formula (III):

(III)

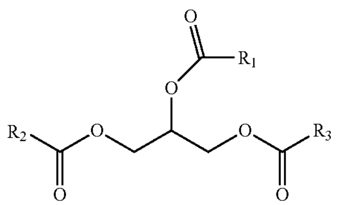

wherein: R1, R2 and R3 are, independently of each other, selected from H and a saturated alkyl chain comprising from 4 to 30 carbon atoms, at least one of R1, R2 and R3 being different from H. According to one embodiment, R1, R2 and R3 are different. Examples include glycerol esters of fatty acid(s) marketed as Nomcort HK-G (INCI name: Glyceryl behenate/eicosadioate) and Nomcort SG (INCI name: Glyceryl tribehenate, isostearate, eicosadioate), by Nisshin Oillio.

Solid Fat

The solid fat at room temperature and pressure is chosen in particular from the group consisting of waxes, pasty fats, butters, and mixtures thereof.

Wax(es)

A "wax", within the meaning of the invention, is a lipophilic compound, solid at room temperature (25° C.), with a reversible solid/liquid change of state, having a melting point greater than or equal to 50° C. and up to 120° C.

The protocol for measuring this melting point is described above.

The waxes that may be used in a dispersion according to the invention may be chosen from solid waxes, deformable or not at room temperature, of animal, vegetable, mineral or synthetic origin and mixtures thereof. Hydrocarbon waxes such as beeswax, lanolin wax, and Chinese insect waxes; rice wax, Carnauba wax, Candellila wax, Ouricurry wax, Alfa wax, cork fibre wax, sugar cane wax, Japan wax and sumac wax are used; montan wax, microcrystalline waxes, paraffins and ozokerite; polyethylene waxes, waxes obtained by the Fisher-Tropsch synthesis and waxy copolymers and their esters. Examples include waxes marketed under the names Kahlwax®2039 (INCI name: *Candelilla cera*) and Kahlwax®6607 (INCI name: *Helianthus Annuus* Seed Wax) by Kahl Wachsraffinerie, Casid HSA (INCI name: Hydroxystearic Acid) by SACI CFPA, Performa®260 (INCI name: Synthetic wax) and Performa®103 (INCI name: Synthetic wax) by New Phase, and AJK-CE2046 (INCI name: Cetearyl alcohol, dibutyl lauroyl glutamide, dibutyl ethylhaxanoyl glutamide) by Kokyu Alcohol Kogyo. Mention may also be made of waxes obtained by catalytic hydrogenation of animal or vegetable oils with linear or branched C8-C32 fatty chains. These include hydrogenated jojoba oil, hydrogenated sunflower oil, hydrogenated castor oil, hydrogenated coconut oil and hydrogenated lanolin oil, di-(1,1,1-trimethylol propane) tetrastearate sold under the name "HEST 2T-4S" by HETERENE, di-(1,1,1-trimethylol propane) tetrabenate sold under the name HEST 2T-4B by HETERENE.

Waxes obtained by transesterification and hydrogenation of vegetable oils, such as castor or olive oil, such as the waxes sold under the names Phytowax castor 16L64® and 22L73® and Phytowax Olive 18L57 by SOPHIM, can also be used. Such waxes are described in application FR2792190.

Silicone waxes can also be used, which can advantageously be substituted polysiloxanes, preferably with low melting points.

Commercial silicone waxes of this type include those sold under the names Abilwax 9800, 9801 or 9810 (GOLDSCHMIDT), KF910 and KF7002 (SHIN ETSU), or 176-1118-3 and 176-11481 (GENERAL ELECTRIC).

Silicone waxes that can be used can also be alkyl or alkoxydimethicones such as the following commercial products: Abilwax 2428, 2434 and 2440 (GOLDSCHMIDT), or VP 1622 and VP 1621 (WACKER), as well as (C20-C60) alkyldimethicones, in particular (C30-C45) alkyldimethicones such as the silicone wax sold under the name SF-1642 by the GE-Bayer Silicones company.

Hydrocarbon waxes modified with silicone or fluorine groups can also be used, for example: Siliconyl candelilla, siliconyl beeswax, and Fluorobeeswax from Koster Keunen.

The waxes may also be selected from fluorinated waxes.

Butter(s) or Pasty Fats

By "butter" (also called "pasty fat") in the sense of the present invention, we mean a lipophilic fatty compound with a reversible solid/liquid change of state and comprising a liquid fraction and a solid fraction at a temperature of 25° C. and at atmospheric pressure (760 mm Hg). In other words, the starting melting temperature of the pasty compound may be below 25° C. The liquid fraction of the pasty compound measured at 25° C. may be from 9% to 97% by weight of the compound. This liquid fraction at 25° C. is preferably between 15% and 85%, preferably between 40 and 85% by weight. Preferably, the butter(s) has (have) a melting end temperature below 60° C. Preferably, the butter(s) have a hardness of less than or equal to 6 MPa.

Preferably, the butters or pasty fats have an anisotropic crystalline organisation in the solid state, visible by X-ray observations.

For the purposes of the invention, the melting point is the temperature of the most endothermic peak observed in thermal analysis (DSC) as described in ISO 11357-3:1999. The melting point of a pasty compound or a wax can be measured using a differential scanning calorimeter (DSC), for example the calorimeter sold as "DSC Q2000" by TA Instruments.

For the measurement of the melting point and the determination of the melting end temperature, the protocols for sample preparation and measurement are as described in WO2017046305.

The liquid fraction by weight of butter (or pasty fat) at 25° C. is equal to the ratio of the enthalpy of fusion consumed at 25° C. to the enthalpy of fusion of the butter. The enthalpy of fusion of a butter or pasty compound is the enthalpy consumed by the compound to change from a solid to a liquid state.

Butter is said to be in a solid state when its entire mass is in solid crystalline form. Butter is said to be in a liquid state when its entire mass is in liquid form. The enthalpy of fusion of the butter is equal to the integral of the whole fusion curve obtained with the aid of the calorimeter referred to, with a temperature rise of 5° C. or 10° C. per minute, according to ISO 11357-3:1999. The enthalpy of fusion of butter is the amount of energy required to bring the compound from a solid to a liquid state. It is expressed in J/g.

The enthalpy of fusion consumed at 25° C. is the amount of energy absorbed by the sample to change from the solid state to the state it has at 25° C. consisting of a liquid and a solid fraction. The liquid fraction of the butter measured at 32° C. preferably represents from 30% to 100% by weight of the compound, preferably from 50% to 100%, more preferably from 60% to 100% by weight of the compound. When the liquid fraction of butter measured at 32° C. is equal to 100%, the temperature of the end of the melting range of the pasty compound is less than or equal to 32° C. The liquid fraction of butter measured at 32° C. is equal to the ratio of the enthalpy of fusion consumed at 32° C. to the enthalpy of fusion of the butter. The enthalpy of fusion consumed at 32° C. is calculated in the same way as the enthalpy of fusion consumed at 23° C.

For hardness measurement, the sample preparation and measurement protocols are as described in WO2017046305.

The pasty fat or butter may be selected from synthetic compounds and compounds of vegetable origin. A pasty fat can be obtained by synthesis from starting materials of vegetable origin.

The pasty fatty substance is advantageously chosen from:

- lanolin and its derivatives such as lanolin alcohol, oxyethylenated lanolins, acetylated lanolin, lanolin esters such as isopropyl lanolate, oxypropylenated lanolins,
- polymeric or non-polymeric silicone compounds such as high molecular weight polydimethysiloxanes, polydimethysiloxanes with alkyl or alkoxy side chains having 8 to 24 carbon atoms, especially stearyl dimethicones,
- polymeric or non-polymeric fluorinated compounds,
- vinyl polymers, in particular
- homopolymers of olefins,
- olefin copolymers,
- homopolymers and copolymers of hydrogenated dienes,
- linear or branched oligomers, homo or copolymers of alkyl (meth)acrylates preferably having a C8-C30 alkyl group,
- homo and copolymeric oligomers of vinyl esters with C8-C30 alkyl groups,
- homo and copolymeric oligomers of vinyl ethers with C8-C30 alkyl groups,
- fat-soluble polyethers resulting from polyetherification between one or more C2-C100, preferably C2-050, diols,
- esters and polyesters, and
- mixtures thereof.

According to a preferred mode of the invention, the particular butter(s) are of vegetable origin such as those described in Ullmann's Encyclopedia of Industrial Chemistry ("Fats and Fatty Oils", A. Thomas, published 15 Jun. 2000, D01: 10.1002/14356007.a10_173, point 13.2.2.2. Shea Butter, *Borneo* Tallow, and Related Fats (Vegetable Butters)).

Particularly noteworthy are C10-C18 triglycerides (INCI name: C10-18 Triglycerides) comprising at the temperature of 25° C. and at atmospheric pressure (760 mm Hg) a liquid fraction and a solid fraction, shea butter, *Nilotica* shea butter (*Butyrospermum parkii*), Galam butter, (*Butyrospermum parkii*) *Borneo* butter or fat or tengkawang tallow (*Shorea stenoptera*), *Shorea* butter, *Illipé* butter, *Madhuca* or *Bassia Madhuca longifolia* butter, Mowrah butter (*Madhuca latifolia*), Katiau butter (*Madhuca mottleyana*), Phulwara butter (*M. butyracea*), mango butter (*Mangifera indica*), *Murumuru* butter (*Astrocatyum murumuru*), Kokum butter (*Garcinia indica*), Ucuuba butter (*Virola sebifera*), *Tucuma* butter, Painya (Kpangnan) butter (*Pentadesma butyracea*), coffee butter (*Coffea arabica*), apricot butter (*Prunus armeniaca*), *Macadamia* butter (*Macadamia temifolia*), grape seed butter (*Vitis vinifera*), avocado butter (*Persea gratissima*), olive butter (*Olea europaea*), sweet almond butter (*Prunus amygdalus dulcis*), cocoa butter (*Theobroma cacao*) and sunflower butter, the butter under the INCI name *Astrocaryum murumuru* Seed Butter, butter with the INCI name *Theobroma grandiflorum* Seed Butter, and butter with the INCI name *Irvingia gabonensis* Kernel Butter, jojoba esters (mixture of wax and hydrogenated jojoba oil) (INCI name: Jojoba esters) and shea butter ethyl esters (INCI name: Shea butter ethyl esters), and mixtures thereof.

According to a particularly preferred embodiment, the lipophilic gelling agent is chosen from Castor Oil/IPDI Copolymer (and) Caprylic/Capric Triglyceride, notably marketed under the name Estogel M by PolymerExpert, Caprylic/Capric Triglyceride (and) Polyurethane-79, in particular marketed under the name OILKEMIA™ 5S polymer by the company Lubrizol, Trihydroxystearin, in particular marketed under the name THIXCIN® R by the company Elementis Specialties, and their mixtures, and better Castor Oil/IPDI Copolymer (and) Caprylic/Capric Triglyceride.

According to a particular embodiment, a dispersion according to the invention, in particular the fatty phase, does not comprise an elastomer gel comprising at least one dimethicone, in particular as marketed by NuSil Technology under the name CareSil™ CXG-1104 (INCI: Dimethicone (and) Dimethicone/Vinyl Dimethicone Crosspolymer).

Preferably, the viscosity of the fatty phase of the drops of a dispersion according to the invention is between 20,000 and 100,000,000 mPa·s, preferably between 50,000 and 1,000,000 mPa·s, and better still between 100,000 and 500,000 mPa·s, at 25° C.

The person skilled in the art will take care to choose the lipophilic gelling agent(s) and/or their quantity in such a way as to satisfy the above-mentioned melting points and physicochemical properties x and y, or even z, of the fatty phase. In particular, the nature and/or quantity of lipophilic gelling agent(s) must take account of the method used (in particular of the "non-microfluidic" or "microfluidic" type) for the manufacture of the dispersion according to the invention. These adjustments are within the competence of the person skilled in the art with regard to the teaching of the present description.

In particular, a dispersion according to the invention may comprise from 0.5% to 30%, preferably from 1% to 25%, in particular from 1.5% to 20%, better from 2% to 15%, and most particularly from 5% to 12%, by weight of lipophilic gelling agent(s) relative to the total weight of the fatty phase.

Preferably, the content of lipophilic gelling agent(s) is greater than or equal to 2%, preferably greater than or equal to 5%, and better still, greater than or equal to 8% by weight, relative to the total weight of the fatty phase.

These percentages refer to the lipophilic gelling agent(s) only present in the dispersed fatty phase.

Oil(s)

In one embodiment, the dispersed fatty phase may comprise at least one oil.

"Oil" means a fatty substance that is liquid at room temperature and atmospheric pressure.

Examples of oils according to the invention include:

- hydrocarbon oils of vegetable origin, as described below;
- hydrocarbon oils of animal origin, such as perhydrosqualene and squalane;
- synthetic esters and ethers, in particular of fatty acids, such as oils of formulae $R_1COOR_2$ and $R_1OR_2$ in which $R_1$ represents the residue of a $C_8$ to $C_{29}$ fatty acid, and $R_2$ represents a $C_3$ to $C_{30}$ hydrocarbon chain, branched or unbranched, such as Purcellin oil, isononyl isononanoate, isodecyl neopentanoate, isostearyl neopentanoate, isopropyl myristate, octyldodecyl myristate, ethyl-2-hexyl palmitate, octyl-2-dodecyl stearate, octyl-2-dodecyl erucate, isostearyl isostearate hydroxy esters such as isostearyl lactate, octylhydroxystearate, octyldodecyl hydroxystearate, diisostearyl malate, triisocetyl citrate, heptanoates, octanoates, decanoates of fatty alcohols; polyol esters, such as propylene glycol dioctanoate, neopentyl glycol diheptanoate and diethylene glycol diisononanoate; and pentaerythritol esters such as pentaerythrityl tetrabenate (DUB PTB) or pentaerythrityl tetraisostearate (Prisorin 3631);

linear or branched hydrocarbons, of mineral or synthetic origin, such as paraffin oils, whether volatile or not, and their derivatives, petroleum jelly, polydecenes, hydrogenated polyisobutene such as Parleam oil;

silicone oils, such as, for example, volatile or non-volatile polymethylsiloxanes (PDMS) with a linear or cyclic silicone chain, which are liquid or pasty at room temperature, in particular cyclopolydimethylsiloxanes (cyclomethicones) such as cyclohexasiloxane and cyclopentasiloxane polydimethylsiloxanes (or dimethicones) containing alkyl, alkoxy or phenyl groups, during or at the end of the silicone chain, groups having from 2 to 24 carbon atoms; phenylated silicones such as phenyltrimethicones, phenyldimethicones, phenyltrimethylsiloxydiphenylsiloxanes, diphenyl-dimethicones, diphenylmethyldiphenyl trisiloxanes, 2-phenylethyltrimethyl-siloxysilicates, and polymethylphenylsiloxanes;

fatty alcohols with 8 to 26 carbon atoms, such as cetyl alcohol, stearyl alcohol and their mixture (cetyl stearyl alcohol), or octyldodecanol;

Partially hydrocarbon and/or silicone fluorinated oils as described in JP-A-2-295912;

and mixtures thereof.

Preferably, the fatty phase of a dispersion according to the invention comprises at least one vegetable oil.

Hydrocarbon oil(s) of vegetable origin include triglycerides of caprylic and capric acids, triglycerides of caprylic, capric, and capric acids (also known as "MCT oil"), myristic and stearic acids (INCI name: Caprylic/capric/myristic/stearic Triglyceride), triethylhexanoine, *Limnanthes alba* seed oil (INCI name: *Limnanthes alba* (Meadowfoam) Seed Oil), *Macadamia* nut oil (INCI name: *Macadamia ternifolia* Seed Oil), *Rosa canina* Rosehip Oil (INCI name: *Rosa canina* Fruit Oil), soybean oil (INCI name: *Glycine soja* (Soybean) Oil), sunflower seed oil (INCI name: *Helianthus annuus* (Sunflower) Seed Oil), tribehenin (INCI name: tribehenin), triisostearin (INCI name: triisostearin), apricot kernel oil (INCI name: *Prunus armeniaca* (Apricot) Kernel Oil), rice bran oil (INCI name: *Oryza sativa* (Rice) Bran Oil), Argan Oil (INCI name: *Argania spinosa* Kernel Oil), avocado oil (INCI name: *Persea gratissima* Oil), Evening Primrose Oil (INCI name: *Oenothera biennis* Oil), rice germ oil (INCI name: *Oryza sativa* Germ Oil), hydrogenated coconut oil (INCI name: Hydrogenated Coconut Oil), sweet almond oil (INCI name: *Prunus amygdalus dulcis* Oil), sesame seed oil (INCI name: *Sesamum indicum* Seed Oil), hydrogenated rapeseed oil (INCI name: Hydrogenated Rapeseed Oil), safflower seed oil (INCI name: *Carthamus tinctorius* Seed Oil), Queensland nut oil *Macadamia integrifolia* (INCI name: *Macadamia integrifolia* Seed Oil), tricaprylin (or triacylglycerol), wheat germ oil (INCI name: *Triticum vulgare* Germ Oil), borage seed oil (INCI name: *Borago officinalis* Seed Oil), shea oil (INCI name: *Butyrospermum parkii* Oil), hydrogenated castor oil (INCI name: Hydrogenated Castor Oil), Chinese Cabbage Seed Oil (INCI name: *Brassica campestris* Seed Oil), *camellia* oil, and in particular Japanese *camellia* seed oil (INCI name: *Camellia japonica* Seed Oil), green tea seed oil (INCI name: *Camellia sinensis* Seed Oil), Sea Buckthorn Oil (INCI name: *Hippophae rhamnoides* Oil), *Camellia kissi* Seed Oil (INCI name: *Camellia kissi* Seed Oil), *Moringa* Seed Oil (INCI name: *Moringa pterygosperma* Seed Oil), canola oil (INCI name: Canola Oil), tea seed oil (INCI name: *Camellia oleifera* Seed Oil), carrot seed oil (INCI name: *Daucus carota sativa* Seed Oil), triheptanoine (INCI name: Triheptanoin), *vanilla* oil (INCI name: *Vanilla planifolia* Fruit Oil), canola oil glycerides and phytosterols (INCI name: Phytosteryl Canola Glycerides), blackcurrant seed oil (INCI name: *Ribes nigrum* (Black Currant) Seed Oil), karanja seed oil (INCI name: *Pongamia glabra* Seed Oil), Roucou Oil (INCI name: Roucou (*Bixa orellana*) Oil), and mixtures thereof.

Preferably, the oil is selected from vegetable oils rich in polyunsaturated fatty acids. For the purposes of this invention, "unsaturated fatty acid" means a fatty acid comprising at least one double bond. According to a preferred embodiment, unsaturated fatty acids with 18 to 22 carbon atoms, in particular polyunsaturated fatty acids, especially ω-3 and ω-6 fatty acids, are used as oil.

Advantageously, the fatty phase comprises at least one oil with a refractive index close to that of the continuous aqueous phase, namely an oil with a refractive index, at room temperature and atmospheric pressure, of preferably between 1.2 and 1.6, preferably between 1.25 and 1.5, in particular between 1.3 and 1.4. This method is advantageous in that it improves the transparency of the fatty phase, and thus the transparency of the dispersion according to the invention. Transparency can be qualified according to the method described in WO2018/167309. Advantageously, the oil with a refractive index between 1.2 and 1.6 is a silicone oil, in particular a phenylated silicone oil.

Advantageously, the fatty phase of a dispersion according to the invention comprises at least one, or even at least two, oil(s), preferably chosen from hydrocarbon oil(s) of vegetable origin, and preferably chosen from *Limnanthes alba* seed oil (INCI name: *Limnanthes alba* (Meadowfoam) Seed Oil, triglycerides of caprylic, capric acids, and a mixture thereof.

Preferably, the oil that may be present in the fatty phase of a dispersion according to the invention is not a silicone oil or a fluorinated oil. Preferably, a dispersion according to the invention, in particular the dispersed fatty phase, does not comprise polydimethylsiloxane (PDMS or dimethicone) or a derivative thereof, and preferably does not comprise silicone oil, and in particular octamethylcyclotetrasiloxane (or Cyclotetrasiloxane or D4), decamethylcyclopentasiloxane (or Cyclopentasiloxane or D5) and Cyclohexasiloxane (or D6).

The person skilled in the art will take care to choose oil(s) and/or their quantity in such a way as to satisfy the abovementioned melting points and physicochemical properties x and y, or even z, of the fatty phase. These adjustments are within the competence of the person skilled in the art with regard to the teaching of the present description.

A dispersion according to the invention may comprise between 10% and 99.5%, preferably between 20% and 90%, more preferably between 30% and 85%, and in particular between 50% and 80%, by weight of oil(s) based on the total weight of the fatty phase.

A dispersion according to the invention may comprise from 1% to 50%, preferably from 5% to 40%, advantageously from 10% to 25% by weight of oil(s) relative to the total weight of said dispersion.

A dispersion according to the invention is also advantageous in that its kinetic stability allows high percentages of dispersed fatty phase. Thus, a dispersion according to the invention may comprise from 1% to 60%, in particular from 5% to 50%, preferably from 10% to 40%, and more preferably from 15% to 30%, by weight of dispersed fatty phase relative to the total weight of the dispersion.

Additional Compound(s)

A dispersion according to the invention, in particular the continuous aqueous phase and/or the dispersed fatty phase, may furthermore comprise at least one additional compound different from the lipophilic gelling agent and the aforementioned oils.

As an additional compound, a dispersion according to the invention, in particular the continuous aqueous phase and/or the dispersed fatty phase, may thus also comprise powders; fillers; flakes; colouring agents, in particular chosen from water-soluble or not, fat-soluble or not, organic or inorganic colouring agents, optical effect materials, liquid crystals, and mixtures thereof; particulate agents insoluble in the fatty phase; preservatives; humectants; perfuming agents, in particular as defined in WO2019002308; stabilizers; chelators; emollients; modifying agents selected from among gelling/texture agents, viscosity agents different from the abovementioned lipophilic gelling agents, and pH, osmotic strength and/or refractive index modifiers etc. or any usual cosmetic additives; and mixtures thereof.

"Fillers" within the meaning of the invention are colourless or white, solid particles of any shape, which are in an insoluble form and dispersed in the medium of the composition. Of a mineral or organic nature, they make it possible to confer body or rigidity and/or softness and uniformity to the deposit, particularly in a make-up context, and improved stability with regard to exudation and non-migration properties after application and/or matting and/or coverage.

For the purposes of the invention, "particulate agents insoluble in the fatty phase" means the group consisting of pigments, ceramics, polymers, particularly acrylic polymers, and mixtures thereof.

As an additional compound, a dispersion according to the invention, in particular the continuous aqueous phase and/or the dispersed fatty phase, may furthermore comprise at least one biological/cosmetic active ingredient, in particular chosen from moisturising agents, healing agents, depigmenting agents, UV filters, desquamating agents, antioxidant agents, active ingredients stimulating the synthesis of dermal and/or epidermal macromolecules, dermodecontracting agents, antiperspirant agents, soothing agents and/or anti-aging agents, and mixtures thereof. Such assets are described in particular in FR1558849 (published as FR3041251A1).

Hydrophilic Gelling Agent(s)

Advantageously, the aqueous phase may further comprise at least one hydrophilic gelling agent, i.e. soluble or dispersible in water. In the context of the present invention, the term "hydrophilic gelling agent" may be used interchangeably with "hydrophilic texturing agent". Hydrophilic gelling agents make it possible to modulate the fluidity of the dispersion, and thus the sensoriality and/or galenic properties, that one wishes to obtain and/or contribute to further improving the kinetic stability of the dispersion.

Hydrophilic gelling agents include:

- natural gelling agents, in particular chosen from among algae extracts, plant exudates, seed extracts and microorganism exudates, such as alkasealan marketed by the company Hakuto (INCI: *Alcaligenes* Polysaccharides), and other natural agents, in particular hyaluronic acid,
- semi-synthetic gelling agents, in particular chosen from cellulose derivatives and modified starches,
- synthetic gelling agents, in particular chosen from homopolymers of (meth)acrylic acid or one of their esters, copolymers of (meth)acrylic acid or one of their esters, copolymers of AMPS (2-acrylamido-2-methylpropane sulphonic acid), associative polymers,
- other gelling agents, in particular selected from polyethylene glycols (marketed under the name Carbowax), clays, silicas such as those marketed under the names Aerosil® 90/130/150/200/300/380), glycerine, and
- mixtures thereof.

By "associative polymer" within the meaning of the present invention is meant any amphiphilic polymer comprising in its structure at least one fatty chain and at least one hydrophilic portion; the associative polymers in accordance with the present invention may be anionic, cationic, nonionic or amphoteric; these are in particular those described in FR2999921. Preferably, these are amphiphilic and anionic associative polymers and amphiphilic and non-ionic associative polymers as described below.

These hydrophilic gelling agents are described in more detail in FR3041251.

According to one embodiment, the dispersion according to the invention comprises from 0.0001% to 20%, preferably from 0.001% to 15%, in particular from 0.01% to 10%, and more preferably from 0.1% to 5%, by weight of hydrophilic gelling agent(s) relative to the total weight of the continuous aqueous phase. These percentages refer to the hydrophilic gelling agent(s) only present in the continuous aqueous phase.

In one embodiment of, the dispersion according to the invention comprises from 0.0001% to 20% by weight, preferably from 0.001% to 15% by weight, and preferentially from 0.01% to 10% by weight of additional compound (s) relative to the total weight of said dispersion.

Of course, the person skilled in the art will take care to choose the possible additional compound(s) and/or their quantity in such a way that the advantageous properties of the dispersion according to the invention, in particular its kinetic stability and, with regard to the dispersed fatty phase, its melting point and its above-mentioned physicochemical properties x and y, or even z, are not or are substantially not altered by the planned addition. In particular, the nature and/or quantity of additional compound(s) depend(s) on the aqueous or fatty nature of the considered phase of the dispersion according to the invention and/or must take into account the method implemented (in particular of the "non-microfluidic" or "microfluidic" type) for the manufacture of the dispersion according to the invention. These choices and adjustments are within the competence of the person skilled in the art.

Preparation Method

A dispersion according to the invention can be prepared by different methods.

Thus, a dispersion according to the invention has the advantage that it can be prepared by a simple "non-microfluidic" method, i.e. by simple emulsification, in particular with the aid of a Rayneri-type stirring device or a paddle stirrer.

As in a conventional emulsion, an aqueous solution and a fatty solution are prepared separately. It is the addition of the fatty phase into the aqueous phase under agitation that creates the direct emulsion.

The viscosity of the aqueous phase can be controlled, in particular, by adjusting the amount of hydrophilic gelling agent and/or the pH of the solution. In general, the pH of the aqueous phase is below 4.5, which may require the addition of a third soda solution (BF) as a last step to reach a pH between 5.5 and 6.5.

The viscosity of the aqueous phase and the shear force applied to the mixture are the two main parameters that influence the size and monodispersity of the drops in the emulsion.

The person skilled in the art will know how to adjust the parameters of the non-microfluidic method in order to achieve the dispersion according to the invention, and in particular to satisfy the desired drop diameter criterion.

The dispersions according to the invention can also be prepared by a microfluidic method, in particular as described in applications WO2012/120043 or WO2019/145424. According to this embodiment, the implemented microfluidic nozzle(s) can have a configuration according to the T-, co-flow, or flow-focusing geometry.

According to this embodiment, the drops obtained by this microfluidic method advantageously have a uniform size distribution.

Preferably, the dispersions of the invention consist of a population of monodisperse drops, in particular such that they have an average diameter $\overline{D}$ of between 100 μm and 3,000 μm, in particular 500 μm to 3,000 μm, and a coefficient of variation Cv of less than 10%, or even less than 3%.

In the context of this description, "monodisperse drops" means that the drop population of the dispersion according to the invention has a uniform size distribution. Monodisperse drops have good monodispersity. Conversely, drops with poor monodispersity are said to be "polydisperse".

According to one mode, the average diameter $\overline{D}$ of the drops is measured, for example, by analysing a photograph of a batch of N drops, by image processing software (Image J). Typically, in this method, the diameter is measured in pixels and then reported in μm, depending on the size of the container containing the drops of the dispersion.

Preferably, the value of N is chosen to be greater than or equal to 30, so that this analysis reflects in a statistically significant way the diameter distribution of the drops of said emulsion. N is advantageously greater than or equal to 100, particularly in the case where the dispersion is polydisperse.

The diameter Di of each drop is measured and the average diameter $\overline{D}$ is obtained by calculating the arithmetic mean of these values:

$$\overline{D} = \frac{1}{N}\sum_{i=1}^{N} D_i$$

From these Di values, the standard deviation a of the drop diameters of the dispersion can also be obtained:

$$\sigma = \sqrt{\frac{\sum_{i=1}^{N}(D_i - \overline{D})^2}{N}}$$

The standard deviation a of a dispersion reflects the distribution of the diameters Di of the drops in the dispersion around the mean diameter $\overline{D}$.

Knowing the mean diameter $\overline{D}$ and the standard deviation a of a dispersion, it can be determined that 95.4% of the drop population is found in the diameter range [$\overline{D}$−2σ;$\overline{D}$+2σ] and 68.2% of the population is found in the range [$\overline{D}$−σ;$\overline{D}$+σ].

To characterize the monodispersity of the dispersion according to this mode of the invention, the coefficient of variation:

$$C_v = \frac{\sigma}{\overline{D}}$$

This parameter reflects the distribution of drop diameters in relation to the average drop diameter.

The coefficient of variation Cv of the diameters of the drops according to this mode of the invention is less than 10%, preferably less than 5%, or even less than 3%.

Alternatively, monodispersity can be demonstrated by placing a dispersion sample in a vial with a constant circular cross-section. Gentle agitation by rotating a quarter-turn for half a second about the axis of symmetry through the bottle, followed by a rest of half a second, is carried out before repeating the operation in the opposite direction four times in succession.

The drops of the dispersed phase are organised in a crystalline form when monodispersed. Thus, they are stacked in a pattern that repeats itself in three dimensions. It is then possible to observe regular stacking, which indicates good monodispersity, and irregular stacking, which indicates polydispersity of the dispersion.

To obtain monodisperse drops, the microfluidic technique can also be used (Utada et al. MRS Bulletin 32, 702-708 (2007); Cramer et al. Chem. Eng. Sci. 59, 15, 3045-3058 (2004)), and more specifically co-flow (fluids go in the same direction) or flow-focusing (fluids go in different directions, and typically in opposite directions) microfluidic systems.

The presence of lipophilic gelling agent(s) in the dispersed fatty phase, or even hydrophilic gelling agent(s) in the continuous aqueous phase, may require adjustments to the method for preparing a dispersion according to the invention. In particular, the method for preparing such a dispersion according to the invention comprises a step of heating (between 50° C. and 150° C., in particular between 60° C. and 90° C.) at least the fatty phase before mixing/contacting said fatty phase with the aqueous phase and, if necessary, maintaining this heating (i) during stirring in the case of a "non-microfluidic" method or (ii) at the level of the microfluidic system in the case of a "microfluidic" method, until the desired dispersion is obtained.

The method for preparing a dispersion of the invention comprises at least the following steps:

a) heating an oil fluid Fl to a temperature of 50° C. to 150° C., preferably 60° C. to 120° C., and more preferably 70° C. to 100° C.;
b) optionally heating an aqueous fluid FE to a temperature of 50° C. to 150° C., preferably 60° C. to 120° C., and more preferably 70° C. to 100° C.;
c) bringing the aqueous fluid FE and the oily fluid Fl into contact; and
d) forming drops of fatty phase, consisting of the oily fluid Fl, dispersed in a continuous aqueous phase, consisting of aqueous fluid FE, wherein:

the oily fluid Fl comprises at least one lipophilic gelling agent and optionally at least one oil and has a melting point between 50° C. and 100° C., preferably between 60° C. and 90° C., and, at room temperature and atmospheric pressure, meets the following physico-chemical criteria:

a hardness (x) of between 2 and 14 N, preferably between 2.5 and 12 N, more preferably between 3 and 9 N, and most preferably between 4 and 6 N; and an adhesiveness (y) greater than or equal to −2 N, and better still, greater than or equal to −1 N, and in particular greater than or equal to −0.6 N;

the oily fluid Fl furthermore being free of amodimethicone and, optionally, further comprising at least one additional compound as mentioned above; and the aqueous fluid FE comprises at least water and, optionally, at least one additional compound as mentioned above, and preferably at least one hydrophilic gelling agent.

Steps (c) and (d) are carried out at a temperature equal to or above the melting point of said gelling agent(s) used. In other words, steps (c) and (d) are carried out with an oily fluid Fl in a form capable of emulsifying with the aqueous fluid FE, and thus capable of ensuring the formation of the drops, and in particular with an oily fluid Fl in liquid form.

According to one embodiment, the fluid Fl is initially prepared by mixing a fatty phase intended to form the core of the drops, comprising at least one lipophilic gelling agent and optionally at least one oil and further optionally at least one additional compound as above.

According to one embodiment, the fluid FE is initially prepared by mixing an aqueous phase intended to form the continuous phase of the dispersion with, optionally, at least one base, at least one additional compound, preservatives and/or other water-soluble products such as glycerine, and most particularly at least one hydrophilic gelling agent.

In one embodiment, the continuous aqueous phase of the dispersion formed comprises, or is represented by, the aqueous fluid FE.

According to one embodiment, the method of making a dispersion according to the invention may further comprise a step e) of injecting a viscosity-increasing solution of the continuous aqueous phase of the FE fluid, for example as described in WO2015/055748. Preferably, the viscosity increasing solution is aqueous. This viscosity-increasing solution is typically injected into the aqueous fluid FE after the formation of the dispersion according to the invention, and thus after the formation of the drops.

According to one embodiment, the viscosity increasing solution comprises a base, in particular an alkali hydroxide, such as sodium hydroxide.

In the case of a "non-microfluidic" method as mentioned above, step c) is represented by agitation during which heating can be maintained during agitation to obtain the desired dispersion.

In the case of a "microfluidic" method as mentioned above, the microfluidic system as such can be adapted to be maintained at a temperature of between 50° C. and 150° C., preferably 80° C. to 90° C.

In the case of a "microfluidic" method, the drop formation step d) may comprise the formation of drops of oily fluid Fl at the outlet of a first conduit opening into the aqueous fluid FE. Preferably, the aqueous fluid FE is circulated in a second conduit, the outlet of the first conduit opening into the second conduit, advantageously coaxially with the local axis of the second conduit.

Advantageously, a method of the invention may comprise, after step d) but before step e), a cooling step f) to accelerate the cooling kinetics of the formed dispersion, and thus prevent the risks of coalescence and fragmentation of the post-formed drops (between 10 and 30° C.).

The present invention also relates to a dispersion obtainable by a method such as those described above.

Uses

Preferably, a dispersion according to the invention can be used directly, after the above-mentioned preparation methods, as a composition, in particular a cosmetic composition. The dispersion according to the invention, when prepared by means of a microfluidic process as described above, can also be used as a composition, in particular a cosmetic composition, after separation of the drops and redispersion of the latter in a suitable second phase.

The invention further relates to the use of a dispersion according to the invention for the preparation of a composition, in particular a cosmetic, pharmaceutical, nutritional or agri-food composition, preferably a cosmetic composition and in particular a composition for caring for and/or making up a keratinous material, in particular the skin.

The present invention thus also relates to a composition, in particular a cosmetic composition, in particular a composition for caring for and/or making up a keratinous material, in particular the skin and/or the hair, and more particularly the skin, comprising at least one dispersion according to the invention, optionally in combination with at least one physiologically acceptable medium.

The dispersions or compositions according to the invention can therefore be used in particular in the cosmetic field.

They may include, in addition to the above-mentioned ingredients or compounds, at least one physiologically acceptable medium.

The physiologically acceptable medium is generally adapted to the nature of the substrate to which the composition is to be applied, as well as to the appearance in which the composition is to be packaged.

In one embodiment, the physiologically acceptable medium is represented directly by the continuous aqueous phase as described above.

In the context of the invention, and unless otherwise stated, "physiologically acceptable medium" means a medium suitable for cosmetic applications, and suitable in particular for the application of a composition of the invention to keratinous material, in particular the skin and/or hair, and more particularly the skin.

The cosmetic compositions of the invention can be, for example, a cream, a lotion, a serum and a gel for the skin (hands, face, feet, etc.), a foundation (liquid, paste), a bath and shower preparation (salts, foams, oils, gels, etc.), a hair care product (hair dyes and bleaches), a cleaning product (lotions, powders, shampoos), a hair cleansing product (lotions, creams, oils,), a hairstyling product (lotions, hairsprays, glosses, etc.), a shaving product (soaps, foams, lotions, etc.), a product to be applied on the lips, a sun product, a sunless tanning product, a skin whitening product, and an anti-wrinkle product. In particular, the cosmetic compositions of the invention may be an anti-ageing serum, a youth serum, a moisturising serum, or a perfumed water.

Thus, in view of the foregoing, a dispersion or composition according to the invention is oral or topical, preferably topical, and more preferably topical on a keratinous material, in particular the skin, and more preferably the skin of the face.

The present invention also relates to a non-therapeutic method for the cosmetic treatment of a keratinous material, in particular the skin and/or the hair, and more particularly the skin, comprising a step of applying to said keratinous material at least one dispersion or at least one cosmetic composition mentioned above.

The present invention also relates to the use of a dispersion or composition according to the invention, to improve the surface appearance of the skin, in particular to moisturise the skin and/or reduce fine lines and wrinkles.

Throughout the description, the phrase "comprising a" is to be understood as synonymous with "comprising at least one", unless otherwise specified. The terms "between . . . and . . . ", "from . . . to . . . " and "ranging from . . . to . . . " shall be understood to include the low and high figures, unless otherwise specified. The amounts of the ingredients in the examples are expressed as a percentage by weight relative to the total weight of the composition, unless otherwise stated.

The following examples illustrate the present invention without limiting its scope.

EXAMPLES

Example 1: Physicochemical Study of Fatty Phases Comprising at Least One Lipophilic Gelling Agent This example consisted of preparing thirteen anhydrous gels that could form the dispersed fatty phase of a dispersion according to the invention, and evaluating their physicochemical properties in terms of hardness (or firmness) (x), adhesiveness (y) and cohesiveness (z). These anhydrous gels differ essentially in the nature of the oil solvent and/or lipophilic gelling agent (e.g. Rheopearl D2 (equivalent to Rheopearl KL2), Estogel M or OILKEMIA™ 5S polymer) and their concentrations (e.g. 5%, 10% and 15%). In the case of Rheopearl D2, test 1D differs from test 10 in the nature of the solvent. Table 1 below shows the composition of these different anhydrous gels.

TABLE 1

| Name | INCI | 1A/1B/1C % w/w | 2A/2B/2C % w/w | 3A/3B/3C % w/w | 4 % w/w | 5 % w/w | 6 % w/w | 1D % w/w |
|---|---|---|---|---|---|---|---|---|
| Labrafac CC | Caprylic/Capric triglyceride | | QSF* | | 0 | QSF* | | 0 |
| DUB Inin | Isononyl Isononanoate | | 0 | | QSF* | 0 | 0 | QSF* |
| Meadowfoam oil | *Limnanthes alba* seed oil | | 15.00 | | 18.00 | 0 | 0 | 15.00 |
| Lipex 205 | *Butyrospermum Parkii* (Shea) Butter | | 0 | | 0 | 15 | 0 | 0 |
| BLANOVA COCONUT OIL REFINED DEODORISED | *COCOS NUCIFERA* OIL | | 0 | | 0 | 0 | 25 | 0 |
| Rheopearl D2 | Dextrin palmitate, Palmitic Acid, Aqua | 05/10/2015 | 0 | 0 | 20 | 0 | 0 | 15 |
| EMC30 | Castor Oil/IPDI Copolymer (and) Caprylic/Capric Triglyceride | 0 | 16.66/33.33/49.99** | 0 | 0 | 33.33 | 33.33 | 0 |
| OILKEMIA ™ 5S polymer | Caprylic/Capric Triglyceride (and) Polyurethane-79 | 0 | 0 | 05/10/2015 | 0 | 0 | 0 | 0 |
| NATPURE COL RED LC318L | *Helianthus Annuus* Seed Oil, CI 40800 | | 0.012 | | 0 | 0 | 0 | 0.012 |
| Total | | | | 100 | | | | |

*QSF: quantity sufficient for

**EMC30 is a premix of Estogel M (INCI: Castor Oil/IPDI Copolymer (and) Caprylic/Capric Triglyceride) in Caprylic/Capric Triglyceride oil in a ratio of 30/70; the corresponding concentrations of lipophilic gelling agent (i.e. Estogel M) are therefore 5%/10%/15% respectively based on the total weight of the anhydrous gel.

The protocol for the preparation of these anhydrous gels is as follows.

Mixture A: the dye (when present) is pre-dispersed in a portion of the Labrafac CC or DUB Inin. The mixture is heated to 50° C. and mixed with a magnetic stirrer.

Mixture B: the remaining solvent (Labrafac CC or DUB Inin) is stirred and heated to 80° C./90° C. depending on the gelling agent to be dispersed; the lipophilic gelling agent (e.g. Estogel M, Rheopearl D2 or OILKEMIA™ 5S polymer) is added under magnetic stirring at 80° C./90° C. until a homogeneous solution is obtained guaranteeing a good dispersion of the polymer.

Mixture C: under hot agitation (80° C./90° C.), Meadowfoam oil or Lipex 205 or Coconut oil is added to mixture B.

Final mixture: under hot agitation (80° C./90° C.), mixture A is added to mixture C.

The melting points of the anhydrous gels are measured as described above and are shown in Table 2 below.

TABLE 2

| Anhydrous gels | 1A | 1B | 1C | 1D | 2A | 2B | 2C | 3A | 3B | 3C | 4 | 5 | 6 |
|---|---|---|---|---|---|---|---|---|---|---|---|---|---|
| Melting point (in ° C.) | 48.3 | 74 | 82.5 | 60.1 | 58.9 | 68.9 | 76.6 | 56 | 67.8 | 76 | 78 | 64 | 65 |

The physicochemical criteria x, y and z of the anhydrous gels are then measured using the texturometer protocol described above. It should be noted that it is not possible to measure the hardness of the fatty phases in example 18 of US 2004/137020 and example 31 of EP 2 189 081. These fatty phases are too hard for the Shimadzu EZ-X texturometer, which has a maximum hardness of 50 N.

The corresponding measurements are shown in FIGS. 1 to 7.

Figure 5:
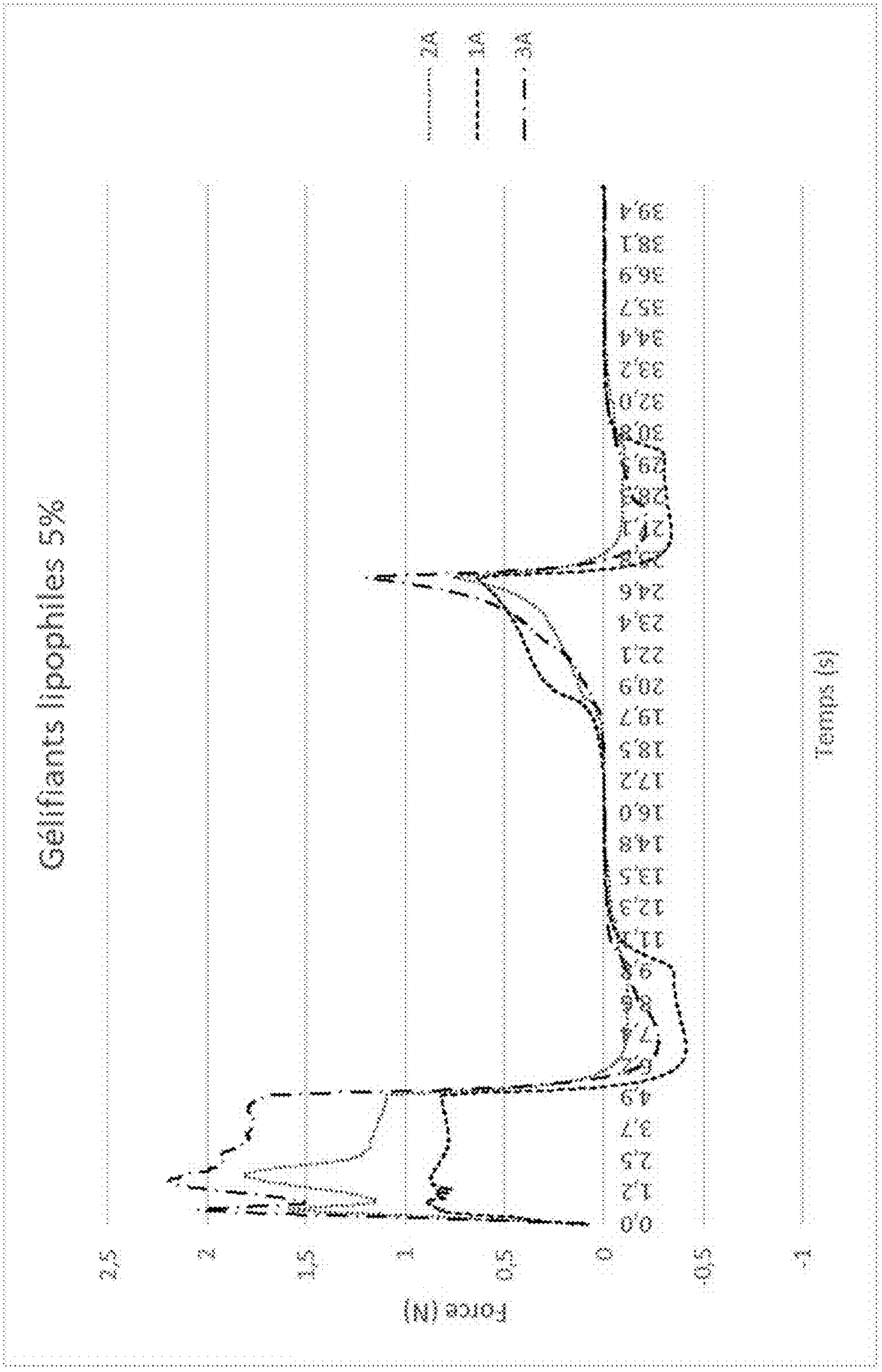
Figure 6:
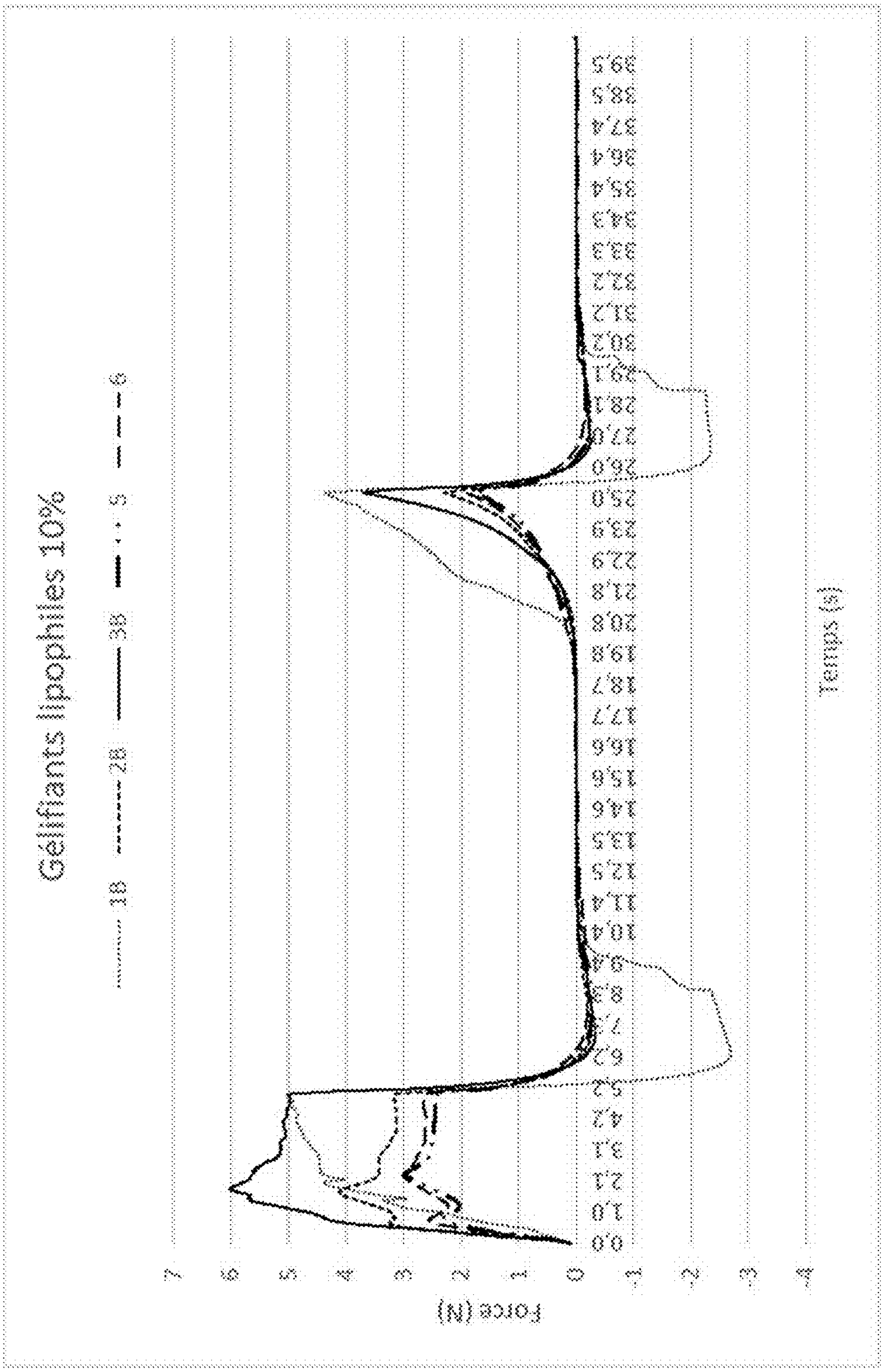
Figure 7:
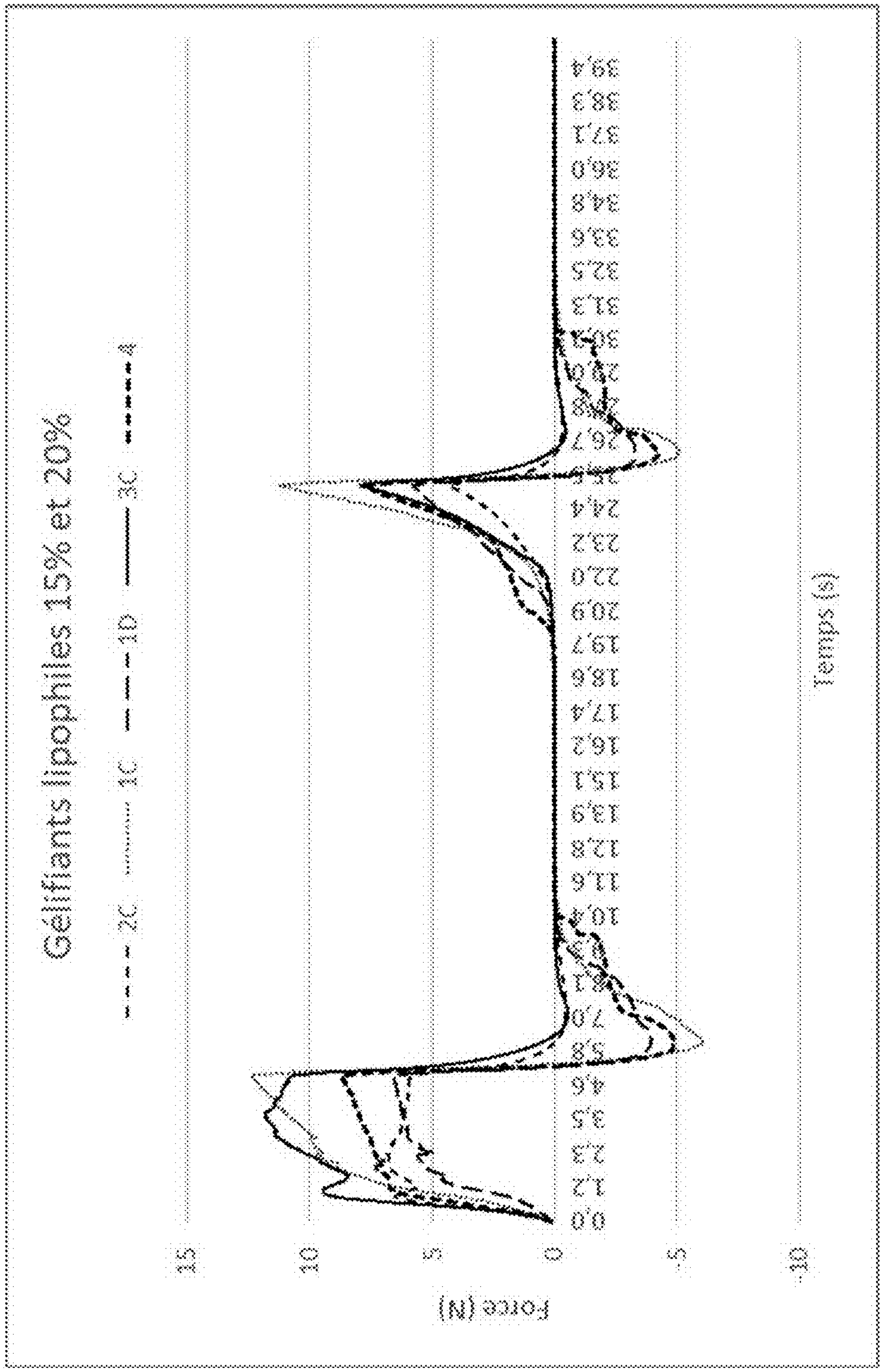

Finally, FIGS. 5 to 7 are graphs representing the texturometry curves of the anhydrous gels in Table 1. These FIGS. 5 to 7 show the force (in N) of the gels in Table 1 as a function of the time (in seconds) during which the gels are subjected to (1) a first compression step (0 to 5 s) and then (2) a second relaxation step where the mobile rises (5 to 10 s). The previous steps (1) and (2) are repeated. These FIGS. 5 to 7 therefore provide information on the physicochemical properties of the gels in Table 1, particularly in terms of hardness, adhesiveness and cohesiveness.

Figure 1:
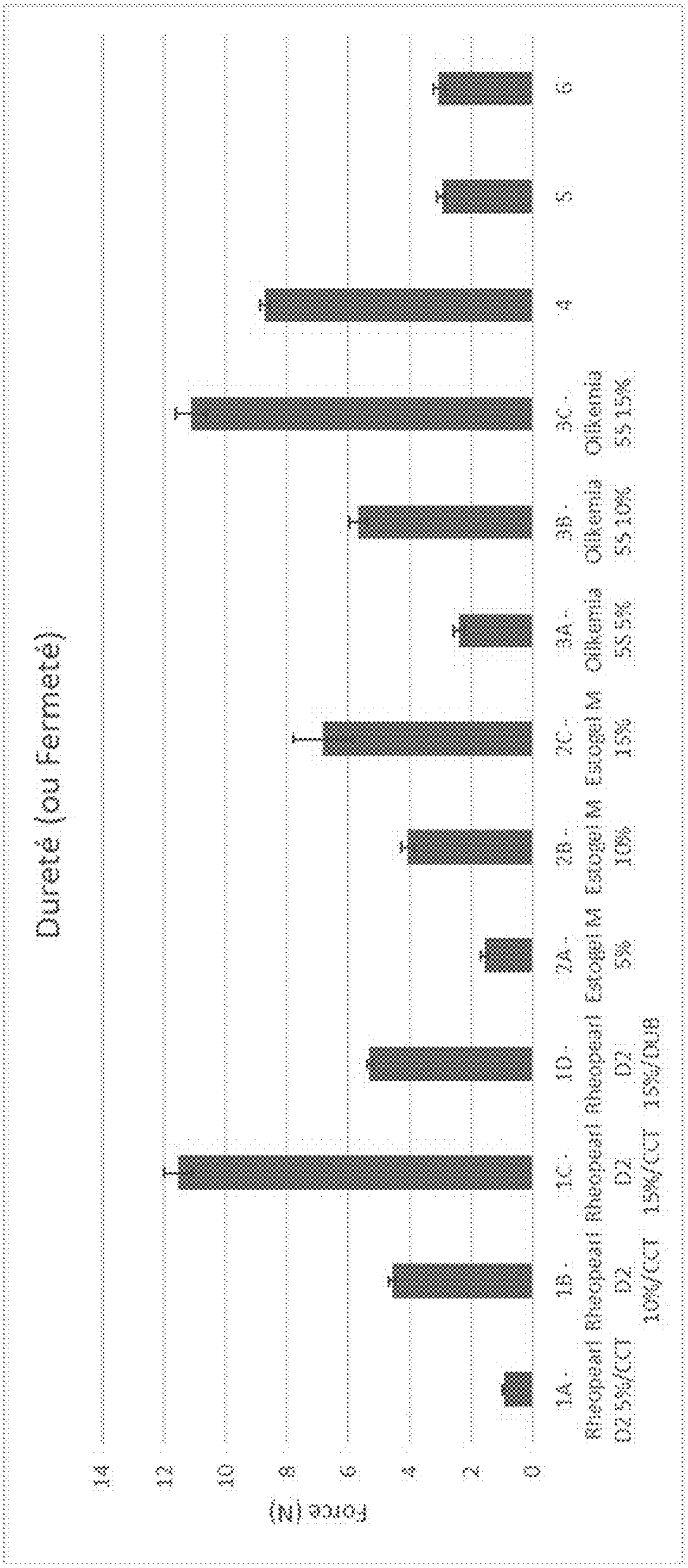
FIG. 1 is a graph representing the hardness criterion (x) of the anhydrous gels in Table 1.
Figure 2:
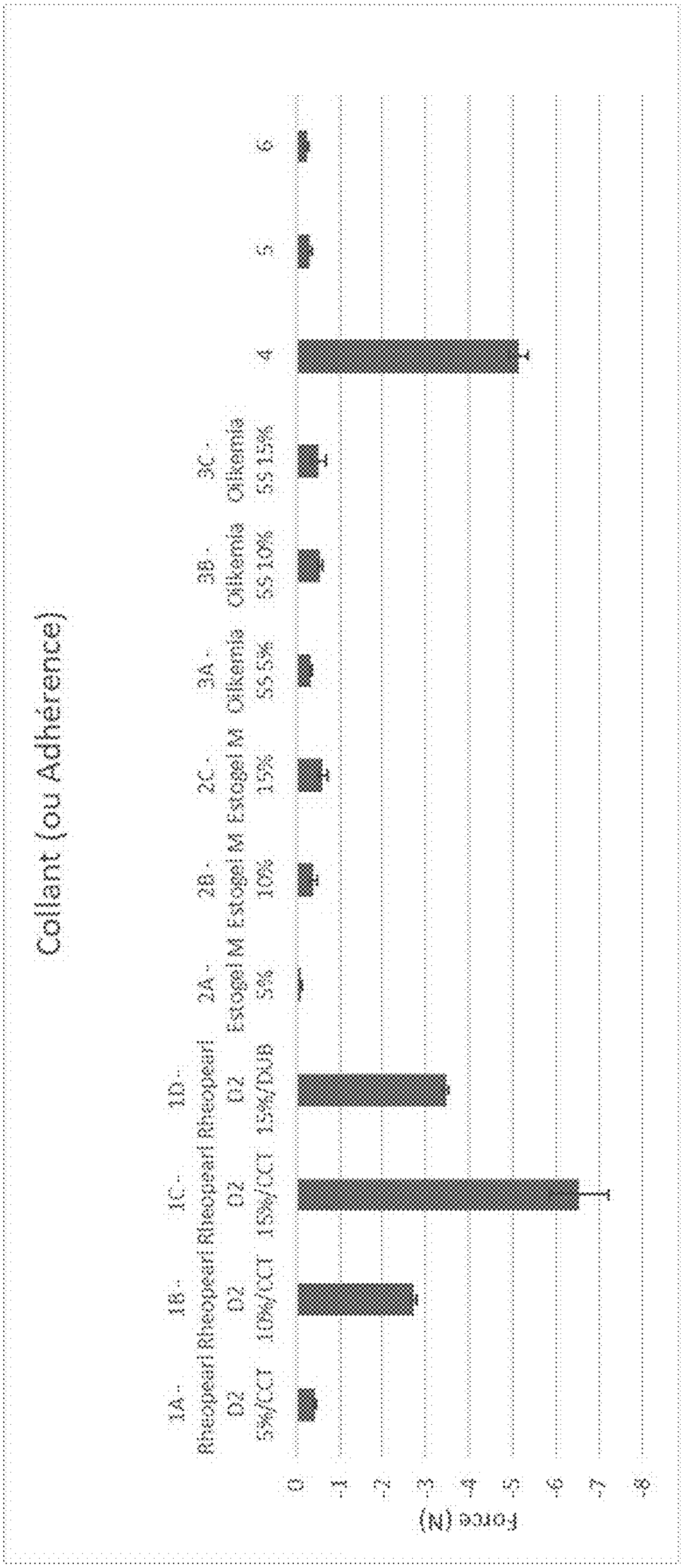
FIG. 2 is a graph representing the adhesiveness criterion (y) of the anhydrous gels in Table 1.
Figure 3:
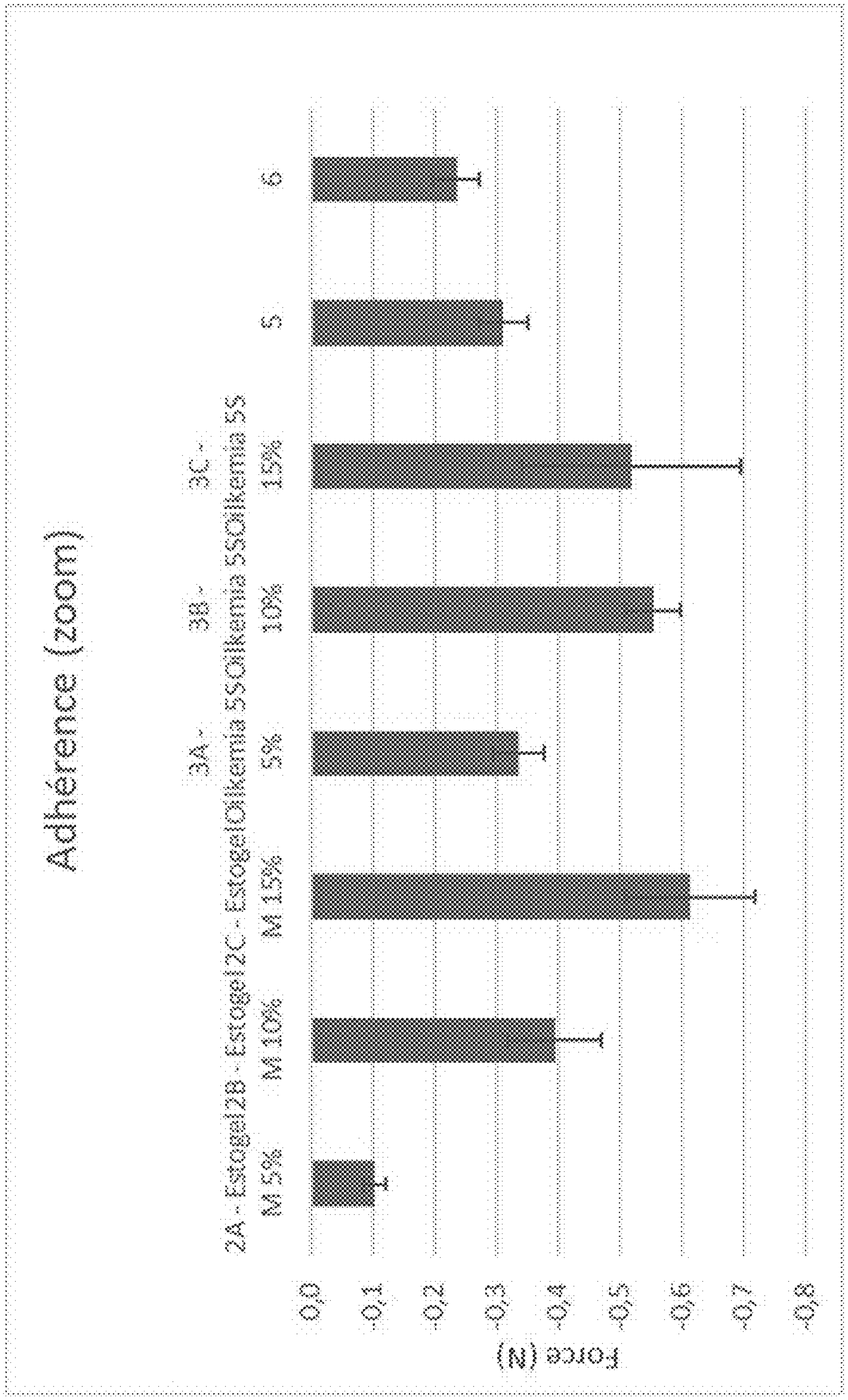
FIG. 3 is an enlargement of FIG. 2 of the adhesiveness values (y) of the anhydrous gels 2A, 2B, 2C, 3A, 3B, 3C, 5 and 6.

Results:

Hardness (x): as shown in FIG. 1, with the same percentage of lipophilic gelling agent and oil solvent (e.g. 1B vs 2B vs 3B), the differences in the hardness profiles of the different anhydrous gels tested are not significant. Furthermore, from tests 1C and 1D, it can be seen that the hardness is impacted by the nature of the solvent. Adhesiveness (y): As shown in FIGS. 2 and 3, with the same percentage of lipophilic gelling agent and oil solvent:

gels 2 (A, B, C), 3 (A, B, C), 5 and 6 have similar adhesiveness profiles, and gels 1 (B, C) and 4 show significantly better adhesiveness than gels 2 (A, B, C) and 3 (A, B, C).

Furthermore, from tests 1C and 1 D, it is observed that the nature of the solvent has an impact on the tackiness.

Figure 4:
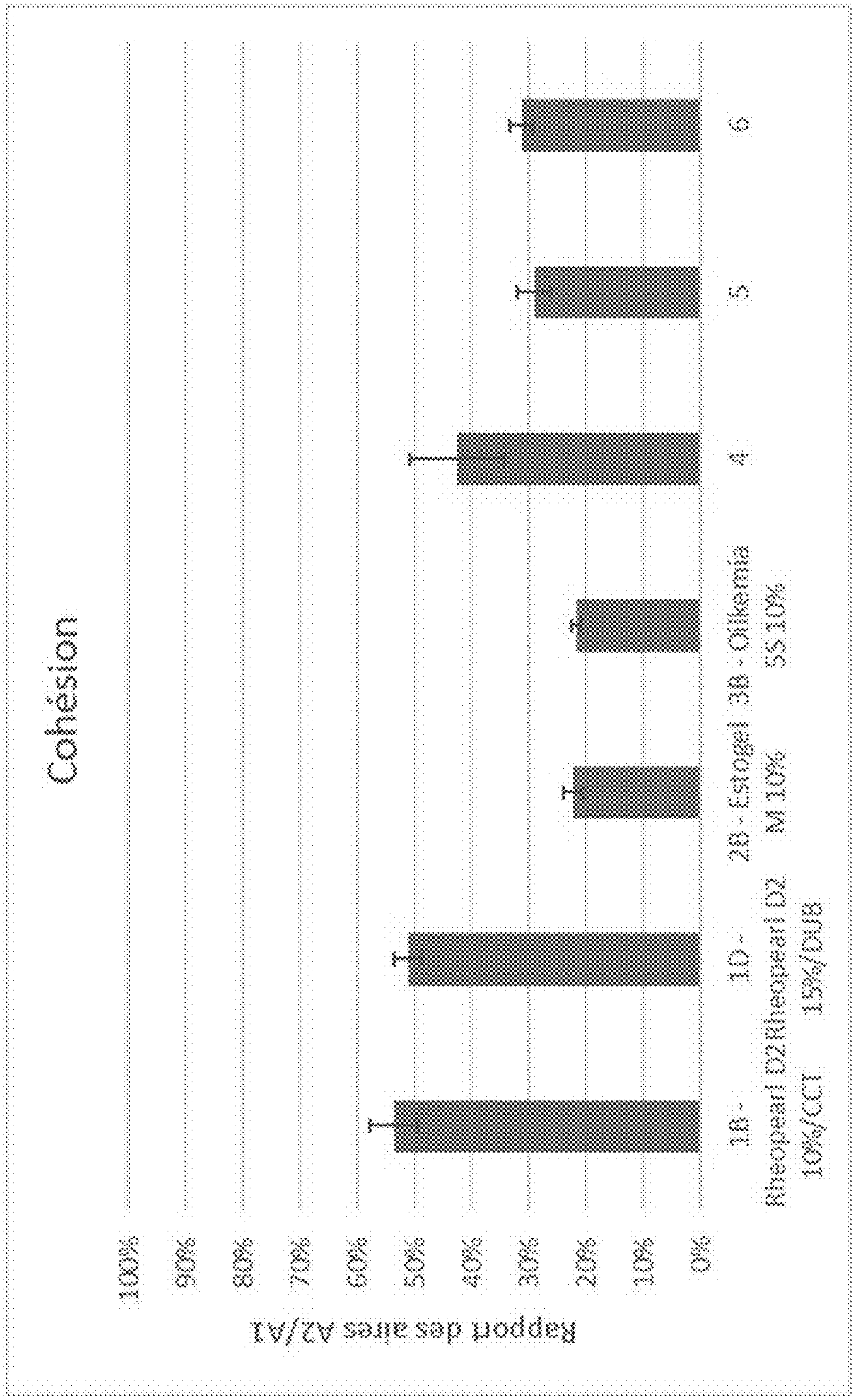
FIG. 4 is a graph showing the cohesiveness criterion (z) of the anhydrous gels 1B, 1D, 2B, 3B, 5 and 6 from Table 1.

Cohesiveness (z): As shown in FIG. 4, gels 2B, 3B, 5 and 6 show similar physicochemical properties in terms of cohesiveness, which are significantly lower than those of gels 1B and 1 D.

Example 2: Preparation of Macroscopic Dispersions

In this example 2, ten dispersions are prepared comprising a continuous aqueous phase and a dispersed phase in the form of drops, each represented by one of the anhydrous gels of example 1. These dispersions are obtained using a microfluidic manufacturing method as described in WO2015/055748. The microfluidic system used is divided into two parts, a first part in which the fatty phase (also designated IF or FI) and the aqueous phase (also designated OF or FE) are brought into contact at high temperature (between 70 and 90° C.) in order to form the dispersion, and a second part which ensures rapid cooling of the dispersion formed in order to accelerate the kinetics of gelling of the drops and thus prevent the risks of coalescence and fragmentation of the drops after formation (between 10 and 30° C.).

The compositions of the phases (fluids) for the preparation of the dispersions are described in Table 3 below.

TABLE 3

| Fluid | Name | INCI | % w/w Phases | % w/w final |
|---|---|---|---|---|
| IF (gelled fatty phase) | Anhydrous gel according to example 1 | | — | 10 |
| OF (continuous aqueous phase) | Osmosis water | Aqua | Qsf* | Qsf* |
| | Microcare PE | Phenoxyethanol, aqua | 0.99 | 0.80 |
| | Microcare emollient PTG | Pentylene glycol, aqua | 2.47 | 2.00 |
| | Glycerine codex | Glycerin, aqua | 9.88 | 8.00 |
| | Zemea Propanediol | Propanediol, aqua | 8.64 | 7.00 |
| | Butylene Glycol 1.3 | Butylene glycol, aqua | 6.17 | 5.00 |
| | Edeta BD | Disodium EDTA | 0.05 | 0.04 |
| | Carbopol ETD 2050 polymer | Carbomer | 0.33 | 0.27 |
| | Carbopol Ultrez 10 polymer | Carbomer | 0.10 | 0.08 |
| | Blanose CMC 7HF | Cellulose, aqua | 0.04 | 0.03 |
| | Sodium hydroxide pellets PRS codex | Sodium hydroxide | 0.01 | 0.01 |
| | Total | | 100 | 81 |
| BF (base) | Osmosis water | Aqua | Qsf | Qsf |
| | Sodium hydroxide pellets PRS codex | Sodium hydroxide | 0.64 | 0.06 |
| | Total | | 100 | 9 |

*QSF: quantity sufficient for

Preparation Protocol:

For the OF:

Mixture A: while stirring in a deflocculator, Phenoxyethanol, Pentylene glycol and EDTA are incorporated into water and the resulting mixture is stirred for 5 min.

Mixture B: Carbopol Ultrez 10 polymer carbomer is then sprinkled onto mixture A until hydrated, then stirred for 30 minutes with a paddle.

Mixture C: Carbopol ETD 2050 polymer is then dispersed in mixture B while stirring for 30 minutes using a paddle.

Mixture D: while stirring in a deflocculator, humectants (i.e. glycerine, zemea propanediol and butylene glycol 1.3) are added to mixture C. The resulting mixture D is kept stirring for 10 min.

Mixture E: the blanose, previously predispersed at 1% in water under magnetic stirring at 80° C., after returning to room temperature, is added to mixture D while stirring in a deflocculator.

Mixture F: soda is added to mixture E which is stirred for 10 minutes to obtain the OF solution.

The OF solution is then introduced into an sOF syringe connected to a heater to keep the OF hot (80° C.).

For IFs: see protocol described in example 1.

Each of the ten heated IF solutions is then introduced into an sIF syringe connected to a heater to keep the IF hot (80° C.). To reduce heat loss, the microfluidic system was installed directly at the outlet of the sIF and sOF syringes and is itself maintained at 80° C.

For BF: soda and water are mixed with the aid of a magnetic bar for 5 min. The BF solution is then introduced into an sBF syringe.

Using the sIF, sOF and SBF syringes and associated syringe plungers, the IF and OF are injected into the microfluidic system and the BF is injected into the dispersion at the outlet of the microfluidic system, at the flow rates described in Table 4 below.

TABLE 4

| Phase | Flow rate per nozzle (in mL/hr) |
|---|---|
| OF | 100 |
| IF | 13.56 |
| BF | 11.11 |

Depending on the configuration of the microfluidic system and the flow rates, the dispersions obtained may comprise drops with a satisfactory monodispersity and with an average diameter between 100 μm and 1500 μm, in particular between 700 and 1300 μm.

Results on the Manufacture of Dispersions:

It was possible to make dispersions from the ten anhydrous gels according to example Stability Test Each of the ten dispersions is then packed into three 30 mL polypropylene (PP) containers, each half filled. After 1 day at room temperature, each test undergoes one of the following three transport tests (one receptacle per test):

roller test (i.e. horizontal circular motion): Wheaton reference, for 1 hour vibration table (i.e. vertical circular motion): reference Heidolph Unimax 1010, for 1 hour; and 3D mixer (i.e. random movements): for 6 minutes.

At the end of these stability tests, the following are evaluated: (i) the integrity of the drops, in particular their fragmentation and (ii) the turbidity of the gel, generally linked to a transfer of the fatty phase into the continuous aqueous phase.

Scoring Criteria:

TABLE 5

| SCORING CRITERIA | 0 | 1 | 2 | 3 |
|---|---|---|---|---|
| BUBBLE FRAG-MENTATION | No frag-mentation | Slight frag-mentation | Average frag-mentation | High frag-mentation |
| GEL TURBIDITY | Clear gel | Slightly cloudy gel | Medium cloudy gel | Cloudy gel |

Results:

TABLE 6

| Dispersion* | D1A | D1B | D1C | D1D | D2A | D2B | D2C | D3A | D3B | D3C | 4 | 5 | 6 |
|---|---|---|---|---|---|---|---|---|---|---|---|---|---|
| bubble fragmentation | 3 | 1 | 0 | 1 | 3 | 1 | 0 | 2 | 1 | 0 | 0 | 2 | 2 |
| Gel turbidity | 3 | 1 | 0 | 1 | 3 | 1 | 0 | 2 | 1 | 0 | 0 | 2 | 2 |
| Conclusion | KO | OK | KO | OK | KO | OK | OK | OK | OK | OK | OK | OK | OK |

*D1A = dispersion according to example 2 using the anhydrous gel 1A of example 1 as the dispersed fatty phase.

The dispersions D1A and D2A show unsatisfactory stability results. The corresponding fatty phases are therefore excluded from the rest of the study. The D3A dispersion shows average stability results but is considered satisfactory enough to be retained for further study. The other dispersions tested showed satisfactory stability results. These results show that a fatty phase must have properties in terms of hardness greater than 2 N, preferably greater than or equal to 2.5 N, in particular greater than or equal to 3 N, and better still, greater than or equal to 4 N.

Sensory Testing

Then, based on the above eight dispersions with satisfactory stability, visual and sensory tests were carried out on a cohort of 24 women aged between 22 and 45. Each woman blindly tested the eight dispersions that were satisfactory in terms of kinetic stability. The criteria evaluated are (i) the adhesion of the dispersed fatty phase drops onto the packaging wall, (ii) the aggregation of the dispersed phase drops with each other and the ease (or comfort) of application, and in particular the ease of crushing and spreading the dispersed phase drops.

Scoring Criteria:

TABLE 7

| SCORING CRITERIA | 0 | 1 | 2 | 3 |
|---|---|---|---|---|
| ADHESION = adhesiveness (y) | Lack of adhesion | Slight adhesion | Average adhesion | Strong adhesion |
| AGGREGATION = cohesiveness (z) | Lack of aggregation | Slight aggregation | Average aggregation | Strong aggregation |
| EASE OF APPLICATION | Very satisfactory application. The drops are not (or only slightly) felt and the mixing between the aqueous and fatty phases is easy. | Satisfactory application. The drops are not or only slightly felt and the mixing between the aqueous and fatty phases is easy. | Moderately satisfactory application. The drops are felt and their crushing on the skin generates lumps. The application of dispersion remains possible. | Unsatisfactory application. The drops are felt and their crushing on the skin generates lumps that are difficult to remove by spreading on the skin. The hardness of the drops is too high. |

Results:

TABLE 8

| Dispersion* | D1B | D1C | D1D | D2B | D2C | D3A | D3B | D3C | 4 | 5 | 6 |
|---|---|---|---|---|---|---|---|---|---|---|---|
| Adhesion = adhesiveness (y) | 3 | 3 | 3 | 0 | 1 | 0 | 1 | 1 | 3 | 0 | 0 |
| Aggregation = cohesiveness (z) | 2 | NR** | 2 | 1 | NR** | NR** | 1 | NR** | 2 | & | & |
| Ease of application | 1 | 2 | 1 | 1 | 2 | 0 | 1 | 2 | 3 | 1 | 1 |

*D1A = dispersion according to example 2 implementing the anhydrous gel 1A of example 1 as the dispersed fatty phase.

**NR: No information.

A fatty phase is observed:

in view of the above results in terms of "ease of application" and FIG. 1, must have a hardness (x) of 14 N or less, preferably 12 N or less, and preferably 9 N or less, in view of the above results in terms of "adhesion" and of FIGS. 2 and 3, that the fatty phase must have a adhesiveness (y) greater than or equal to −2 N, and better still, greater than or equal to −1 N, or even greater than or equal to −0.6 N, and in view of the above results in terms of "aggregation" and FIG. 4, that the fatty phase must have a cohesiveness (z) of less than or equal to 40, preferably less than or equal to 35, and better still, less than or equal to 30.

Conclusion

In view of the above results, it is observed that a dispersion comprising a dispersed phase comprising drops and a continuous aqueous phase, when the stability of this dispersion is not ensured by the presence of a shell at the "continuous aqueous phase/dispersed fatty phase" interface or of surfactant, can nevertheless and unexpectedly present satisfactory properties in terms of kinetic stability and sensoriality, in particular in terms of comfort and ease of application, on the condition that the gelled fatty phase has:

(i) a melting point between 50° C. and 100° C., preferably between 60° C. and 90° C., and, (ii) at room temperature and atmospheric pressure:

a hardness (x) of between 2 and 14 N, in particular between 2.5 and 12 N, preferably between 3 and 9 N, and more preferably between 4 and 6 N;

an adhesiveness (y) greater than or equal to −2 N, and better still, greater than or equal to −1 N, and in particular greater than or equal to −0.6 N; and optionally, a cohesiveness (z) of less than or equal to 40, preferably less than or equal to 35, and better still, less than or equal to 30.

Even more unexpectedly, these results are observed and applicable with a dispersion with dispersed fatty phase drops of macroscopic size.

What is claimed is:

1. A dispersion comprising a dispersed phase comprising drops and a continuous aqueous phase, wherein the drops comprise a fatty phase comprising at least one lipophilic gelling agent, wherein:

the fatty phase has a melting point between 50° C. and 100° C. and, at room temperature and atmospheric pressure, meets the following physicochemical criteria:

a hardness (x) of between 2 and 14 N;

an adhesiveness (y) greater than or equal to −2 N; and the dispersion does not comprise amodimethicone.

2. The dispersion according to claim 1, wherein the fatty phase has a cohesiveness (z) of less than or equal to 40.

3. The dispersion according to claim 1, wherein the dispersion does not comprise a shell.

4. The dispersion according to claim 1, wherein the drops in the dispersed phase have a diameter greater than or equal to 100 μm and represent a volume greater than or equal to 60% of a total volume of the dispersed phase, and/or at least 60% of the drops in the dispersed phase have an average diameter greater than or equal to 100 um.

5. The dispersion according to claim 1, wherein the lipophilic gelling agent is selected from organic or inorganic, polymeric or molecular lipophilic gelling agents; solid fats at ambient temperature and pressure; and mixtures thereof.

6. The dispersion according to claim 1, comprising from 0.5% to 30% by weight of lipophilic gelling agent(s) relative to a total weight of the fatty phase.

7. The dispersion of claim 1, wherein the continuous aqueous phase comprises at least one hydrophilic gelling agent.

8. The dispersion according to claim 7, comprising from 0.0001% to 20% by weight of hydrophilic gelling agent(s) based on a total weight of the continuous aqueous phase.

9. The dispersion of claim 1, comprising from 1% to 60% by weight of dispersed fatty phase relative to a total weight of the dispersion.

10. The dispersion of claim 1, wherein the dispersion does not comprise surfactants.

11. The dispersion of claim 1, wherein the dispersion does not comprise: dextrin ester and fatty acid(s), hydrophobically treated silica, acrylates/C10-30 alkyl acrylate crosspolymer, and/or cetyl ethylhexanoate.

12. A method of preparing a dispersion according to claim 1, comprising at least the following steps:

a) heating an oily fluid to a temperature from 50° C. to 150° C.;

b) optionally heating an aqueous fluid to a temperature from 50° C. to 150° C.;

c) bringing the aqueous fluid and the oily fluid into contact; and d) forming drops of fatty phase, consisting of the oily fluid, dispersed in a continuous aqueous phase, consisting of aqueous fluid, wherein:

the oily fluid comprises at least one lipophilic gelling agent and optionally at least one oil and has a melting point between 50° C. and 100° C., and, at room temperature and atmospheric pressure, meets the following physicochemical criteria:

a hardness (x) of between 2 and 14 N;

an adhesiveness (y) greater than or equal to −2 N;

the oil fluid further being free of amodimethicone; and the aqueous fluid comprises at least water and, optionally, at least one hydrophilic gelling agent.

13. The method according to claim 12, wherein step d comprises forming drops of oily fluid at an outlet of a first conduit opening into the aqueous fluid.

14. The method according to claim 13, where in aqueous fluid is circulated in a second conduit, the outlet of the first conduit opening into the second conduit.

15. A dispersion obtained by a method according to claim 12.

16. A composition comprising at least one dispersion of claim 1, optionally in combination with at least one physiologically acceptable medium.

17. A non-therapeutic method for a cosmetic treatment of a keratinous material, comprising a step of applying at least one dispersion to said keratinous material, according to claim 1.

18. A non-therapeutic method for a cosmetic treatment of a keratinous material, comprising a step of applying to said keratinous material a composition according to claim 16.

* * * * *